United States Patent
Daly et al.

(10) Patent No.: US 7,396,664 B2
(45) Date of Patent: Jul. 8, 2008

(54) VEGF-BINDING FUSION PROTEINS AND NUCLEIC ACIDS ENCODING THE SAME

(75) Inventors: Thomas J. Daly, New City, NY (US); Nicholas J. Papadopoulos, LaGrangeville, NY (US); Margaret Karow, Putnam Valley, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 297 days.

(21) Appl. No.: 11/204,709

(22) Filed: Aug. 16, 2005

(65) Prior Publication Data

US 2006/0058234 A1    Mar. 16, 2006

Related U.S. Application Data

(60) Continuation-in-part of application No. 11/016,097, filed on Dec. 17, 2004, and a continuation-in-part of application No. 11/016,503, filed on Dec. 17, 2004, which is a division of application No. 10/009,852, filed as application No. PCT/US00/14142 on May 23, 2000, now Pat. No. 7,070,959, application No. 11/204,709, and a continuation-in-part of application No. 10/880,021, filed on Jun. 29, 2004, now Pat. No. 7,279,159, which is a continuation-in-part of application No. 10/609,775, filed on Jun. 30, 2003, now Pat. No. 7,087,411, which is a continuation-in-part of application No. 10/009,852, filed on Dec. 6, 2001, now Pat. No. 7,070,959.

(60) Provisional application No. 60/138,133, filed on Jun. 8, 1999.

(51) Int. Cl.
*C12N 15/62* (2006.01)
*C12N 15/63* (2006.01)
*A61K 38/18* (2006.01)
*C07K 14/00* (2006.01)
*C07K 14/71* (2006.01)

(52) U.S. Cl. ............... 435/69.7; 424/134.1; 424/192.1; 435/71.1; 435/252.3; 435/320.1; 435/325; 435/358; 514/2; 514/12; 530/350; 530/387.3; 536/23.4

(58) Field of Classification Search ............. None
See application file for complete search history.

(56) References Cited

U.S. PATENT DOCUMENTS 6,897,294 B2    5/2005    Davis-Smyth et al.

FOREIGN PATENT DOCUMENTS

WO    WO 00/75319    12/2000

OTHER PUBLICATIONS

Davis-Smyth et al. (1996). The second immunoglobulin-like domain of the VEGF tyrosine kinase receptor Flt-1 determines ligand binding and may initiate a signal transduction cascade. The EMBO Journal. 15(18):4919-4927.*
Davis-Smyth, T., et al, (1998) J. Bio. Chem. 273(6):3216-3222.
Heidaran, M., et al., (1990) J. Bio. Chem. 265(31):18741-18744.
Holash, J., et al., (2002) PNAS 99(17):11393-11398.
Heidaran, M., et al., (1995) FASEB J. 9:140-145.
Wulff, C., et al., (2002) Endocrinology 143(7):2797-2807.

* cited by examiner

*Primary Examiner*—Christine J Saoud
*Assistant Examiner*—Jon M Lockard
(74) *Attorney, Agent, or Firm*—Valeta Gregg, Esq.

(57) ABSTRACT

Nucleic acid molecules and multimeric proteins capable of binding vascular endothelial growth factor (VEGF). VEGF traps are disclosed which are therapeutically useful for treating VEGF-associated conditions and diseases, and are specifically designed for local administration to specific organs, tissues, and/or cells.

11 Claims, 3 Drawing Sheets

| Observed Masses | | Expected Masses | Monosaccharide Compositions | Proposed Sugar Chain Structures |
|---|---|---|---|---|
| VGT C04003 M500 | VGT C04008 M500 | | | |
| 1356.4 | 1356.0 | 1356.1 | (Man)2(Man)3(Glc)2 | |
| 1380.9 | 1381.6 | 1381.2 | (Glc)(Man)3(Glc)2(Fuc) | |
| 1397.2 | 1397.2 | 1397.3 | (Gal)(Glc)(Man)3(Glc)2 | |
| 1438.6 | 1438.2 | 1438.2 | (Glc)2(Man)3(Glc)2 | |
| 1526.7 | 1525.9 | 1527.2 | (Glc)(Man)3(Glc)2(Fuc) | |
| 1543.4 | 1542.8 | 1543.4 | (Gal)(Glc)(Man)3(Glc)2(Fuc) | |
| 1559.7 | 1559.4 | 1559.4 | (Gal)(Glc)(Man)(Man)3(Glc)2 | |
| 1584.6 | 1584.0 | 1584.4 | (Glc)2(Man)3(Glc)2(Fuc) | |
| 1600.5 | 1600.0 | 1600.4 | (Gal)(Glc)2(Man)3(Glc)2 | |
| 1646.5 | 1646.6 | | | Adduct of 1584.4 |
| 1688.5 | 1688.0 | 1688.4 | (SA)(Gal)(Glc)(Man)3(Glc)2 | |
| 1721.5 | 1720.8 | 1721.5 | (Gal)(Glc)(Man)2(Man)3(Glc)2 | |

Figure 1A

| Observed Masses | | Expected Masses | Monosaccharide Compositions | Proposed Sugar Chain Structures |
|---|---|---|---|---|
| VGT C04003 M500 | VGT C04008 M500 | | | |
| 1746.7 | 1746.2 | 1746.5 | (Gal)(Glc)2(Man)3(Glc)2(Fuc) |  |
| 1762.8 | 1762.6 | 1762.1 | (Gal)2(Glc)2(Man)3(Glc)2 |  |
| 1809.5 | 1809.1 | | | Adduct of 1746.5 |
| 1834.8 | 1834.7 | 1834.5 | (SA)(Gal)(Glc)(Man)3(Glc)2(Fuc) |  |
| 1849.9 | 1851.0 | 1850.5 | (SA)(Gal)2(Glc)(Man)3(Glc)2 | |
| 1891.9 | 1891.1 | 1891.6 | (SA)(Gal)(Glc)2(Man)3(Glc)2 |  |
| 1908.6 | 1908.2 | 1908.6 | (Gal)(Glc)2(Man)3(Glc)2(Fuc) |  |
| 1996.9 | 1996.5 | 1996.6 | (SA)(Gal)2(Glc)(Man)3(Glc)2(Fuc) |  |
| 2012.8 | 2012.3 | 2012.8 | (SA)(Gal) (Glc)2(Glc)2(Man)3(Glc)2 | |
| 2037.7 | 2037.3 | 2037.7 | (SA)(Gal)2(Glc)2(Man)3(Glc)2(Fuc) |  |
| 2053.8 | 2053.2 | 2053.8 | (SA)(Gal)2(Glc)2(Man)3(Glc)2 |  |
| 2075.8 | 2074.9 | | | Adduct of 2053.8 |
| 2116.0 | 2115.7 | | | Adduct of 2053.8 |

| Observed Masses | | Expected Masses | Monosaccharide Compositions | Proposed Sugar Chain Structures |
|---|---|---|---|---|
| VGT C04003 M500 | VGT C04008 M500 | | | |
| 2200.0 | 2199.3 | 2199.9 | (SA)(Gal)2(Glc)2(Man)3(Glc)2(Fuc) | |
| 2221.5 | 2221.5 | | | Na+ Adduct of 2199.9 |
| 2262.5 | 2261.3 | | | Adduct of 2199.9 |
| 2345.6 | 2345.6 | 2345.0 | (SA)2(Gal)2(Glc)2(Man)3(Glc)2 | |
| 2407.0 | 2407.2 | | | Adduct of 2345.0 |
| 2492.5 | 2492.0 | 2491.2 | (SA)2(Gal)2(Glc)2(Man)3(Glc)2(Fuc) | |
| 2554.3 | 2553.1 | | | Adduct of 2491.2 |
| 2564.6 | 2564.0 | 2565.2 | (SA)(Gal)3(Glc)3(Man)3(Glc)2(Fuc) | |
| 2857.2 | 2857.3 | 2856.5 | (SA)2(Gal)3(Glc)3(Man)3(Glc)2(Fuc) | |
| 2918.1 | 2918.9 | | | Adduct of 2856.5 |
| 3148.5 | 3148.5 | 3147.8 | (SA)3(Gal)3(Glc)3(Man)3(Glc)2(Fuc) | |
| 3211.0 | 3211.0 | | | Adduct of 3147.8 |

Figure 1C

SEQUENCE LISTING

```
<160> NUMBER OF SEQ ID NOS: 24

<210> SEQ ID NO 1
<211> LENGTH: 4
<212> TYPE: PRT
<213> ORGANISM: homo sapiens

<400> SEQUENCE: 1

Cys Pro Pro Cys
 1

<210> SEQ ID NO 2
<211> LENGTH: 200
<212> TYPE: PRT
<213> ORGANISM: homo sapiens

<400> SEQUENCE: 2

Met Gly Arg Pro Phe Val Glu Met Tyr Ser Glu Ile Pro Glu Ile Ile
 1               5                  10                  15

His Met Thr Glu Gly Arg Glu Leu Val Ile Pro Cys Arg Val Thr Ser
            20                  25                  30

Pro Asn Ile Thr Val Thr Leu Lys Lys Phe Pro Leu Asp Thr Leu Ile
        35                  40                  45

Pro Asp Gly Lys Arg Ile Ile Trp Asp Ser Arg Lys Gly Phe Ile Ile
    50                  55                  60

Ser Asn Ala Thr Tyr Lys Glu Ile Gly Leu Leu Thr Cys Glu Ala Thr
65                  70                  75                  80

Val Asn Gly His Leu Tyr Lys Thr Asn Tyr Leu Thr Gln Thr Asn Thr
                85                  90                  95

Ile Ile Asp Val Val Leu Ser Pro Ser His Gly Ile Glu Leu Ser Val
            100                 105                 110

Gly Glu Lys Leu Val Leu Asn Cys Thr Ala Arg Thr Glu Leu Asn Val
        115                 120                 125

Gly Ile Asp Phe Asn Trp Glu Tyr Pro Ser Ser Lys His Gln His Lys
```

```
            130                 135                 140
Lys Leu Val Asn Arg Asp Leu Lys Thr Gln Ser Gly Ser Glu Met Lys
145                 150                 155                 160

Lys Phe Leu Ser Thr Leu Thr Ile Asp Gly Val Thr Arg Ser Asp Gln
                165                 170                 175

Gly Thr Cys Ala Ala Ser Ser Gly Leu Met Thr Lys Lys Asn Ser Thr
            180                 185                 190

Phe Val Arg Val His Glu Lys Cys
                195                 200

<210> SEQ ID NO 3
<211> LENGTH: 4
<212> TYPE: PRT
<213> ORGANISM: homo sapiens

<400> SEQUENCE: 3

Ala Cys Gly Cys
 1

<210> SEQ ID NO 4
<211> LENGTH: 203
<212> TYPE: PRT
<213> ORGANISM: homo sapiens

<400> SEQUENCE: 4

Met Gly Arg Pro Phe Val Glu Met Tyr Ser Glu Ile Pro Glu Ile Ile
 1               5                  10                  15

His Met Thr Glu Gly Arg Glu Leu Val Ile Pro Cys Arg Val Thr Ser
                20                  25                  30

Pro Asn Ile Thr Val Thr Leu Lys Lys Phe Pro Leu Asp Thr Leu Ile
            35                  40                  45

Pro Asp Gly Lys Arg Ile Ile Trp Asp Ser Arg Lys Gly Phe Ile Ile
    50                  55                  60

Ser Asn Ala Thr Tyr Lys Glu Ile Gly Leu Leu Thr Cys Glu Ala Thr
65                  70                  75                  80

Val Asn Gly His Leu Tyr Lys Thr Asn Tyr Leu Thr Gln Thr Asn Thr
                85                  90                  95

Ile Ile Asp Val Val Leu Ser Pro Ser His Gly Ile Glu Leu Ser Val
            100                 105                 110

Gly Glu Lys Leu Val Leu Asn Cys Thr Ala Arg Thr Glu Leu Asn Val
        115                 120                 125

Gly Ile Asp Phe Asn Trp Glu Tyr Pro Ser Ser Lys His Gln His Lys
    130                 135                 140

Lys Leu Val Asn Arg Asp Leu Lys Thr Gln Ser Gly Ser Glu Met Lys
145                 150                 155                 160

Lys Phe Leu Ser Thr Leu Thr Ile Asp Gly Val Thr Arg Ser Asp Gln
                165                 170                 175

Gly Thr Cys Ala Ala Ser Ser Gly Leu Met Thr Lys Lys Asn Ser Thr
            180                 185                 190

Phe Val Arg Val His Glu Lys Ala Cys Gly Cys
                195                 200

<210> SEQ ID NO 5
<211> LENGTH: 1453
<212> TYPE: DNA
<213> ORGANISM: homo sapiens

<400> SEQUENCE: 5
```

```
aagcttgggc tgcaggtcga tcgactctag aggatcgatc cccgggcgag ctcgaattcg      60
caaccaccat ggtcagctac tgggacaccg gggtcctgct gtgcgcgctg ctcagctgtc     120
tgcttctcac aggatctagt tccggaggta gacctttcgt agagatgtac agtgaaatcc     180
ccgaaattat acacatgact gaaggaaggg agctcgtcat tccctgccgg gttacgtcac     240
ctaacatcac tgttacttta aaaaagtttc cacttgacac tttgatccct gatgaaaaac     300
gcataatctg ggacagtaga aagggcttca tcatatcaaa tgcaacgtac aaagaaatag     360
ggcttctgac ctgtgaagca acagtcaatg gcatttgta taagacaaac tatctcacac     420
atcgacaaac caatacaatc atagatgtgg ttctgagtcc gtctcatgga attgaactat     480
ctgttggaga aaagcttgtc ttaaattgta cagcaagaac tgaactaaat gtggggattg     540
acttcaactg gaatacccct tcttcgaagc atcagcataa gaaacttgta aaccgagacc     600
taaaaaccca gtctgggagt gagatgaaga aattttttgag caccttaact atagatggtg     660
taacccggag tgaccaagga ttgtacacct gtgcagcatc cagtgggctg atgaccaaga     720
agaacagcac atttgtcagg gtccatgaaa agggcccggg cgacaaaact cacacatgcc     780
caccgtgccc agcacctgaa ctcctggggg gaccgtcagt cttcctcttc cccccaaaac     840
ccaaggacac cctcatgatc tcccggaccc ctgaggtcac atgcgtggtg gtggacgtga     900
gccacgaaga ccctgaggtc aagttcaact ggtacgtgga cggcgtggag gtgcataatg     960
ccaagacaaa gccgcgggag gagcagtaca acagcacgta ccgtgtggtc agcgtcctca    1020
ccgtcctgca ccaggactgg ctgaatggca aggagtacaa gtgcaaggtc tccaacaaag    1080
ccctcccagc ccccatcgag aaaaccatct ccaaagccaa agggcagccc cgagaaccac    1140
aggtgtacac cctgccccca tcccgggatg agctgaccaa gaaccaggtc agcctgacct    1200
gcctggtcaa aggcttctat cccagcgaca tcgccgtgga gtgggagagc aatgggcagc    1260
cggagaacaa ctacaagacc acgcctcccg tgctggactc cgacggctcc ttcttcctct    1320
atagcaagct caccgtggac aagagcaggt ggcagcaggg gaacgtcttc tcatgctccg    1380
tgatgcatga ggctctgcac aaccactaca cgcagaagag cctctccctg tctccgggta    1440
aatgagcggc cgc                                                        1453
```

<210> SEQ ID NO 6
<211> LENGTH: 458
<212> TYPE: PRT
<213> ORGANISM: homo sapiens

<400> SEQUENCE: 6

```
Met Val Ser Tyr Trp Asp Thr Gly Val Leu Leu Cys Ala Leu Leu Ser
 1               5                  10                  15

Cys Leu Leu Thr Gly Ser Ser Gly Gly Arg Pro Phe Val Glu
             20                  25                  30

Met Tyr Ser Glu Ile Pro Glu Ile His Met Thr Glu Gly Arg Glu
         35                  40                  45

Leu Val Ile Pro Cys Arg Val Thr Ser Pro Asn Ile Thr Val Thr Leu
     50                  55                  60

Lys Lys Phe Pro Leu Asp Thr Leu Ile Pro Asp Gly Lys Arg Ile Ile
 65                  70                  75                  80

Trp Asp Ser Arg Lys Gly Phe Ile Ile Ser Asn Ala Thr Tyr Lys Glu
                 85                  90                  95

Ile Gly Leu Leu Thr Cys Glu Ala Thr Val Asn Gly His Leu Tyr Lys
            100                 105                 110
```

Thr Asn Tyr Leu Thr His Arg Gln Thr Asn Thr Ile Ile Asp Val Val
            115                 120                 125

Leu Ser Pro Ser His Gly Ile Glu Leu Ser Val Gly Glu Lys Leu Val
        130                 135                 140

Leu Asn Cys Thr Ala Arg Thr Glu Leu Asn Val Gly Ile Asp Phe Asn
145                 150                 155                 160

Trp Glu Tyr Pro Ser Ser Lys His Gln His Lys Lys Leu Val Asn Arg
                165                 170                 175

Asp Leu Lys Thr Gln Ser Gly Ser Glu Met Lys Lys Phe Leu Ser Thr
            180                 185                 190

Leu Thr Ile Asp Gly Val Thr Arg Ser Asp Gln Gly Leu Tyr Thr Cys
        195                 200                 205

Ala Ala Ser Ser Gly Leu Met Thr Lys Lys Asn Ser Thr Phe Val Arg
    210                 215                 220

Val His Glu Lys Gly Pro Gly Asp Lys Thr His Thr Cys Pro Pro Cys
225                 230                 235                 240

Pro Ala Pro Glu Leu Leu Gly Gly Pro Ser Val Phe Leu Phe Pro Pro
                245                 250                 255

Lys Pro Lys Asp Thr Leu Met Ile Ser Arg Thr Pro Glu Val Thr Cys
            260                 265                 270

Val Val Val Asp Val Ser His Glu Asp Pro Glu Val Lys Phe Asn Trp
        275                 280                 285

Tyr Val Asp Gly Val Glu Val His Asn Ala Lys Thr Lys Pro Arg Glu
    290                 295                 300

Glu Gln Tyr Asn Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
                325                 330                 335

Lys Ala Leu Pro Ala Pro Ile Glu Lys Thr Ile Ser Lys Ala Lys Gly
            340                 345                 350

Gln Pro Arg Glu Pro Gln Val Tyr Thr Leu Pro Pro Ser Arg Asp Glu
        355                 360                 365

Leu Thr Lys Asn Gln Val Ser Leu Thr Cys Leu Val Lys Gly Phe Tyr
    370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
                405                 410                 415

Leu Tyr Ser Lys Leu Thr Val Asp Lys Ser Arg Trp Gln Gln Gly Asn
            420                 425                 430

Val Phe Ser Cys Ser Val Met His Glu Ala Leu His Asn His Tyr Thr
        435                 440                 445

Gln Lys Ser Leu Ser Leu Ser Pro Gly Lys
    450                 455

<210> SEQ ID NO 7
<211> LENGTH: 1377
<212> TYPE: DNA
<213> ORGANISM: homo sapiens

<400> SEQUENCE: 7
atggtcagct actgggacac cggggtcctg ctgtgcgcgc tgctcagctg tctgcttctc      60
acaggatcta gttccggaag tgataccggt agacctttcg tagagatgta cagtgaaatc     120

```
cccgaaatta tacacatgac tgaaggaagg gagctcgtca ttccctgccg ggttacgtca    180
cctaacatca ctgttacttt aaaaaagttt ccacttgaca ctttgatccc tgatggaaaa    240
cgcataatct gggacagtag aaagggcttc atcatatcaa atgcaacgta caaagaaata    300
gggcttctga cctgtgaagc aacagtcaat gggcatttgt ataagacaaa ctatctcaca    360
catcgacaaa ccaatacaat catagatgtg gttctgagtc cgtctcatgg aattgaacta    420
tctgttggag aaaagcttgt cttaaattgt acagcaagaa ctgaactaaa tgtggggatt    480
gacttcaact gggaataccc ttcttcgaag catcagcata gaaacttgt aaaccgagac    540 ctaaaaaccc agtctgggag tgagatgaag aaattttga gcaccttaac tatagatggt    600
gtaacccgga gtgaccaagg attgtacacc tgtgcagcat ccagtgggct gatgaccaag    660
aagaacagca catttgtcag ggtccatgaa aaggacaaaa ctcacacatg cccaccgtgc    720
ccagcacctg aactcctggg gggaccgtca gtcttcctct tccccccaaa acccaaggac    780
accctcatga tctcccggac ccctgaggtc acatgcgtgg tggtggacgt gagccacgaa    840
gaccctgagg tcaagttcaa ctggtacgtg gacggcgtgg aggtgcataa tgccaagaca    900
aagccgcggg aggagcagta caacagcacg taccgtgtgg tcagcgtcct caccgtcctg    960
caccaggact ggctgaatgg caaggagtac aagtgcaagg tctccaacaa agccctccca   1020 gccccatcg agaaaccat ctccaaagcc aaagggcagc cccgagaacc acaggtgtac   1080
accctgcccc catcccggga tgagctgacc aagaaccagg tcagcctgac ctgcctggtc   1140
aaaggcttct atcccagcga catcgccgtg gagtgggaga gcaatgggca gccggagaac   1200
aactacaaga ccacgcctcc cgtgctggac tccgacggct ccttcttcct ctacagcaag   1260
ctcaccgtgg acaagagcag gtggcagcag gggaacgtct tctcatgctc cgtgatgcat   1320
gaggctctgc acaaccacta cacgcagaag agcctctccc tgtctccggg taaatga     1377

<210> SEQ ID NO 8
<211> LENGTH: 458
<212> TYPE: PRT
<213> ORGANISM: homo sapiens

<400> SEQUENCE: 8

Met Val Ser Tyr Trp Asp Thr Gly Val Leu Leu Cys Ala Leu Leu Ser
 1               5                   10                  15

Cys Leu Leu Leu Thr Gly Ser Ser Gly Ser Asp Thr Gly Arg Pro
            20                  25                  30

Phe Val Glu Met Tyr Ser Glu Ile Pro Glu Ile Ile His Met Thr Glu
        35                  40                  45

Gly Arg Glu Leu Val Ile Pro Cys Arg Val Thr Ser Pro Asn Ile Thr
    50                  55                  60

Val Thr Leu Lys Lys Phe Pro Leu Asp Thr Leu Ile Pro Asp Gly Lys
65                  70                  75                  80

Arg Ile Ile Trp Asp Ser Arg Lys Gly Phe Ile Ile Ser Asn Ala Thr
                85                  90                  95

Tyr Lys Glu Ile Gly Leu Leu Thr Cys Glu Ala Thr Val Asn Gly His
            100                 105                 110

Leu Tyr Lys Thr Asn Tyr Leu Thr His Arg Gln Thr Asn Thr Ile Ile
        115                 120                 125

Asp Val Val Leu Ser Pro Ser His Gly Ile Glu Leu Ser Val Gly Glu
    130                 135                 140

Lys Leu Val Leu Asn Cys Thr Ala Arg Thr Glu Leu Asn Val Gly Ile
145                 150                 155                 160
```

-continued

```
Asp Phe Asn Trp Glu Tyr Pro Ser Ser Lys His Gln His Lys Lys Leu
            165                 170                 175
Val Asn Arg Asp Leu Lys Thr Gln Ser Gly Ser Glu Met Lys Lys Phe
        180                 185                 190
Leu Ser Thr Leu Thr Ile Asp Gly Val Thr Arg Ser Asp Gln Gly Leu
    195                 200                 205
Tyr Thr Cys Ala Ala Ser Ser Gly Leu Met Thr Lys Lys Asn Ser Thr
210                 215                 220
Phe Val Arg Val His Glu Lys Asp Lys Thr His Thr Cys Pro Pro Cys
225                 230                 235                 240
Pro Ala Pro Glu Leu Leu Gly Gly Pro Ser Val Phe Leu Phe Pro Pro
                245                 250                 255
Lys Pro Lys Asp Thr Leu Met Ile Ser Arg Thr Pro Glu Val Thr Cys
            260                 265                 270
Val Val Val Asp Val Ser His Glu Asp Pro Glu Val Lys Phe Asn Trp
        275                 280                 285
Tyr Val Asp Gly Val Glu Val His Asn Ala Lys Thr Lys Pro Arg Glu
    290                 295                 300
Glu Gln Tyr Asn Ser Thr Tyr Arg Val Val Ser Val Leu Thr Val Leu
305                 310                 315                 320
His Gln Asp Trp Leu Asn Gly Lys Glu Tyr Lys Cys Lys Val Ser Asn
                325                 330                 335
Lys Ala Leu Pro Ala Pro Ile Glu Lys Thr Ile Ser Lys Ala Lys Gly
            340                 345                 350
Gln Pro Arg Glu Pro Gln Val Tyr Thr Leu Pro Pro Ser Arg Asp Glu
        355                 360                 365
Leu Thr Lys Asn Gln Val Ser Leu Thr Cys Leu Val Lys Gly Phe Tyr
    370                 375                 380
Pro Ser Asp Ile Ala Val Glu Trp Glu Ser Asn Gly Gln Pro Glu Asn
385                 390                 395                 400
Asn Tyr Lys Thr Thr Pro Pro Val Leu Asp Ser Asp Gly Ser Phe Phe
                405                 410                 415
Leu Tyr Ser Lys Leu Thr Val Asp Lys Ser Arg Trp Gln Gln Gly Asn
            420                 425                 430
Val Phe Ser Cys Ser Val Met His Glu Ala Leu His Asn His Tyr Thr
        435                 440                 445
Gln Lys Ser Leu Ser Leu Ser Pro Gly Lys
    450                 455
```

<210> SEQ ID NO 9
<211> LENGTH: 1444
<212> TYPE: DNA
<213> ORGANISM: homo sapiens

<400> SEQUENCE: 9

```
aagcttgggc tgcaggtcga tcgactctag aggatcgatc cccgggcgag ctcgaattcg     60
caaccaccat ggtcagctac tgggacaccg gggtcctgct gtgcgcgctg ctcagctgtc    120
tgcttctcac aggatctagt tccggaggta gaccttcgt agagatgtac agtgaaatcc     180
ccgaaattat acacatgact gaaggaaggg agctcgtcat tccctgccgg ttacgtcac    240
ctaacatcac tgttactttta aaaagtttc cacttgacac tttgatccct gatggaaaac    300
gcataatctg ggacagtaga aagggcttca tcatatcaaa tgcaacgtac aaagaaatag    360
ggcttctgac ctgtgaagca acagtcaatg ggcatttgta taagacaaac tatctcacac    420
```

-continued

```
atcgacaaac caatacaatc atagatatcc agctgttgcc caggaagtcg ctggagctgc    480
tggtagggga gaagctggtc ctcaactgca ccgtgtgggc tgagtttaac tcaggtgtca    540
cctttgactg ggactaccca gggaagcagg cagagcgggg taagtgggtg cccgagcgac    600
gctcccaaca gacccacaca gaactctcca gcatcctgac catccacaac gtcagccagc    660
acgacctggg ctcgtatgtg tgcaaggcca caacggcat ccagcgattt cgggagagca    720
ccgaggtcat tgtgcatgaa atggcccgg gcgacaaaac tcacacatgc ccaccgtgcc    780
cagcacctga actcctgggg ggaccgtcag tcttcctctt ccccccaaaa cccaaggaca    840
ccctcatgat ctcccggacc cctgaggtca catgcgtggt ggtggacgtg agccacgaag    900
accctgaggt caagttcaac tggtacgtgg acggcgtgga ggtgcataat gccaagacaa    960
agccgcggga ggagcagtac aacagcacgt accgtgtggt cagcgtcctc accgtcctgc   1020
accaggactg gctgaatggc aaggagtaca agtgcaaggt ctccaacaaa gccctcccag   1080
cccccatcga gaaaaccatc tccaaagcca agggcagcc ccgagaacca caggtgtaca   1140
ccctgccccc atcccgggat gagctgacca agaaccaggt cagcctgacc tgcctggtca   1200
aaggcttcta tcccagcgac atcgccgtgg agtgggagag caatgggcag ccggagaaca   1260
actacaagac cacgcctccc gtgctggact ccgacggctc cttcttcctc tatagcaagc   1320
tcaccgtgga caagagcagg tggcagcagg ggaacgtctt ctcatgctcc gtgatgcatg   1380
aggctctgca caaccactac acgcagaaga gcctctccct gtctccgggt aaatgagcgg   1440
ccgc                                                                  1444
```

<210> SEQ ID NO 10
<211> LENGTH: 455
<212> TYPE: PRT
<213> ORGANISM: homo sapiens

<400> SEQUENCE: 10

```
Met Val Ser Tyr Trp Asp Thr Gly Val Leu Leu Cys Ala Leu Leu Ser
 1               5                  10                  15

Cys Leu Leu Leu Thr Gly Ser Ser Ser Gly Gly Arg Pro Phe Val Glu
            20                  25                  30

Met Tyr Ser Glu Ile Pro Glu Ile Ile His Met Thr Glu Gly Arg Glu
        35                  40                  45

Leu Val Ile Pro Cys Arg Val Thr Ser Pro Asn Ile Thr Val Thr Leu
    50                  55                  60

Lys Lys Phe Pro Leu Asp Thr Leu Ile Pro Asp Gly Lys Arg Ile Ile
65                  70                  75                  80

Trp Asp Ser Arg Lys Gly Phe Ile Ile Ser Asn Ala Thr Tyr Lys Glu
                85                  90                  95

Ile Gly Leu Leu Thr Cys Glu Ala Thr Val Asn Gly His Leu Tyr Lys
            100                 105                 110

Thr Asn Tyr Leu Thr His Arg Gln Thr Asn Thr Ile Ile Asp Ile Gln
        115                 120                 125

Leu Leu Pro Arg Lys Ser Leu Glu Leu Leu Val Gly Glu Lys Leu Val
    130                 135                 140

Leu Asn Cys Thr Val Trp Ala Glu Phe Asn Ser Gly Val Thr Phe Asp
145                 150                 155                 160

Trp Asp Tyr Pro Gly Lys Gln Ala Glu Arg Gly Lys Trp Val Pro Glu
                165                 170                 175

Arg Arg Ser Gln Gln Thr His Thr Glu Leu Ser Ser Ile Leu Thr Ile
```

```
                    180                 185                 190
His Asn Val Ser Gln His Asp Leu Gly Ser Tyr Val Cys Lys Ala Asn
            195                 200                 205

Asn Gly Ile Gln Arg Phe Arg Glu Ser Thr Glu Val Ile Val His Glu
        210                 215                 220

Asn Gly Pro Gly Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Asp Glu Leu Thr Lys
        355                 360                 365

Asn Gln Val Ser Leu Thr Cys Leu Val Lys Gly Phe Tyr Pro Ser Asp
370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys
    450                 455

<210> SEQ ID NO 11
<211> LENGTH: 24
<212> TYPE: DNA
<213> ORGANISM: homo sapiens

<400> SEQUENCE: 11
gggctgttga gagagagaga gagc                                          24

<210> SEQ ID NO 12
<211> LENGTH: 28
<212> TYPE: DNA
<213> ORGANISM: homo sapiens

<400> SEQUENCE: 12
ggccgctctc tctctctctc aacagccc                                      28

<210> SEQ ID NO 13
<211> LENGTH: 23
<212> TYPE: DNA
<213> ORGANISM: homo sapiens
```

```
<400> SEQUENCE: 13
gggcgcatgc ggttgttgag agc                                              23

<210> SEQ ID NO 14
<211> LENGTH: 27
<212> TYPE: DNA
<213> ORGANISM: homo sapiens

<400> SEQUENCE: 14
ggccgctctc aacaaccgca tgcgccc                                          27

<210> SEQ ID NO 15
<211> LENGTH: 36
<212> TYPE: DNA
<213> ORGANISM: homo sapiens

<400> SEQUENCE: 15
gagagagacc atgggtagac ctttcgtaga gatgta                                36

<210> SEQ ID NO 16
<211> LENGTH: 48
<212> TYPE: DNA
<213> ORGANISM: homo sapiens

<400> SEQUENCE: 16
agagaggcgg ccgctttatc aacacttttc atggaccctg acaaatgt                   48

<210> SEQ ID NO 17
<211> LENGTH: 57
<212> TYPE: DNA
<213> ORGANISM: homo sapiens

<400> SEQUENCE: 17
agagaggcgg ccgctttatc aacaaccgca tgccttttca tggaccctga caaatgt        57

<210> SEQ ID NO 18
<211> LENGTH: 235
<212> TYPE: PRT
<213> ORGANISM: homo sapiens

<400> SEQUENCE: 18
```

Met Val Ser Tyr Trp Asp Thr Gly Val Leu Leu Cys Ala Leu Leu Ser
 1               5                  10                  15

Cys Leu Leu Leu Thr Gly Ser Ser Ser Gly Ser Asp Thr Gly Arg Pro
            20                  25                  30

Phe Val Glu Met Tyr Ser Glu Ile Pro Glu Ile Ile His Met Thr Glu
        35                  40                  45

Gly Arg Glu Leu Val Ile Pro Cys Arg Val Thr Ser Pro Asn Ile Thr
    50                  55                  60

Val Thr Leu Lys Lys Phe Pro Leu Asp Thr Leu Ile Pro Asp Gly Lys
65                  70                  75                  80

Arg Ile Ile Trp Asp Ser Arg Lys Gly Phe Ile Ile Ser Asn Ala Thr
                85                  90                  95

Tyr Lys Glu Ile Gly Leu Leu Thr Cys Glu Ala Thr Val Asn Gly His
            100                 105                 110

Leu Tyr Lys Thr Asn Tyr Leu Thr His Arg Gln Thr Asn Thr Ile Ile
        115                 120                 125

Asp Val Val Leu Ser Pro Ser His Gly Ile Glu Leu Ser Val Gly Glu
    130                 135                 140

```
Lys Leu Val Leu Asn Cys Thr Ala Arg Thr Glu Leu Asn Val Gly Ile
145                 150                 155                 160

Asp Phe Asn Trp Glu Tyr Pro Ser Ser Lys His Gln His Lys Lys Leu
                165                 170                 175

Val Asn Thr Gln Ser Gly Ser Glu Met Lys Arg Asp Leu Lys Lys Phe
            180                 185                 190

Leu Ser Thr Leu Thr Ile Asp Gly Val Thr Arg Ser Asp Gln Gly Leu
        195                 200                 205

Tyr Thr Cys Ala Ala Ser Ser Gly Leu Met Thr Lys Lys Asn Ser Thr
    210                 215                 220

Phe Val Arg Val His Glu Lys Gly Pro Gly Cys
225                 230                 235

<210> SEQ ID NO 19
<211> LENGTH: 435
<212> TYPE: PRT
<213> ORGANISM: homo sapiens

<400> SEQUENCE: 19

Met Val Ser Tyr Trp Asp Thr Gly Val Leu Leu Cys Ala Leu Leu Ser
1               5                   10                  15

Cys Leu Leu Leu Thr Gly Ser Ser Ser Gly Ser Asp Thr Gly Arg Pro
            20                  25                  30

Phe Val Glu Met Tyr Ser Glu Ile Pro Glu Ile Ile His Met Thr Glu
        35                  40                  45

Gly Arg Glu Leu Val Ile Pro Cys Arg Val Thr Ser Pro Asn Ile Thr
    50                  55                  60

Val Thr Leu Lys Lys Phe Pro Leu Asp Thr Leu Ile Pro Asp Gly Lys
65                  70                  75                  80

Arg Ile Ile Trp Asp Ser Arg Lys Gly Phe Ile Ile Ser Asn Ala Thr
                85                  90                  95

Tyr Lys Glu Ile Gly Leu Leu Thr Cys Glu Ala Thr Val Asn Gly His
            100                 105                 110

Leu Tyr Lys Thr Asn Tyr Leu Thr His Arg Gln Thr Asn Thr Ile Ile
        115                 120                 125

Asp Val Val Leu Ser Pro Ser His Gly Ile Glu Leu Ser Val Gly Glu
    130                 135                 140

Lys Leu Val Leu Asn Cys Thr Ala Arg Thr Glu Leu Asn Val Gly Ile
145                 150                 155                 160

Asp Phe Asn Trp Glu Tyr Pro Ser Ser Lys His Gln His Lys Lys Leu
                165                 170                 175

Val Asn Arg Asp Leu Lys Thr Gln Ser Gly Ser Glu Met Lys Lys Phe
            180                 185                 190

Leu Ser Thr Leu Thr Ile Asp Gly Val Thr Arg Ser Asp Gln Gly Leu
        195                 200                 205

Tyr Thr Cys Ala Ala Ser Ser Gly Leu Met Thr Lys Lys Asn Ser Thr
    210                 215                 220

Phe Val Arg Val His Glu Lys Gly Pro Gly Arg Pro Phe Val Glu Met
225                 230                 235                 240

Tyr Ser Glu Ile Pro Glu Ile Ile His Met Thr Glu Gly Arg Glu Leu
            245                 250                 255

Val Ile Pro Cys Arg Val Thr Ser Pro Asn Ile Thr Val Thr Leu Lys
        260                 265                 270

Lys Phe Pro Leu Asp Thr Leu Ile Pro Asp Gly Lys Arg Ile Ile Trp
    275                 280                 285
```

```
Asp Ser Arg Lys Gly Phe Ile Ile Ser Asn Ala Thr Tyr Lys Glu Ile
    290                 295                 300

Gly Leu Leu Thr Cys Glu Ala Thr Val Asn Gly His Leu Tyr Lys Thr
305                 310                 315                 320

Asn Tyr Leu Thr His Arg Gln Thr Asn Thr Ile Ile Asp Val Val Leu
                325                 330                 335

Ser Pro Ser His Gly Ile Glu Leu Ser Val Gly Glu Lys Leu Val Leu
            340                 345                 350

Asn Cys Thr Ala Arg Thr Glu Leu Asn Val Gly Ile Asp Phe Asn Trp
        355                 360                 365

Glu Tyr Pro Ser Ser Lys His Gln His Lys Lys Leu Val Asn Arg Asp
370                 375                 380

Leu Lys Thr Gln Ser Gly Ser Glu Met Lys Lys Phe Leu Ser Thr Leu
385                 390                 395                 400

Thr Ile Asp Gly Val Thr Arg Ser Asp Gln Gly Leu Tyr Thr Cys Ala
                405                 410                 415

Ala Ser Ser Gly Leu Met Thr Lys Lys Asn Ser Thr Phe Val Arg Val
            420                 425                 430

His Glu Lys
        435

<210> SEQ ID NO 20
<211> LENGTH: 238
<212> TYPE: PRT
<213> ORGANISM: homo sapiens

<400> SEQUENCE: 20

Met Val Ser Tyr Trp Asp Thr Gly Val Leu Leu Cys Ala Leu Leu Ser
  1               5                  10                  15

Cys Leu Leu Leu Thr Gly Ser Ser Ser Gly Ser Asp Thr Gly Arg Pro
                20                  25                  30

Phe Val Glu Met Tyr Ser Glu Ile Pro Glu Ile Ile His Met Thr Glu
            35                  40                  45

Gly Arg Glu Leu Val Ile Pro Cys Arg Val Thr Ser Pro Asn Ile Thr
    50                  55                  60

Val Thr Leu Lys Lys Phe Pro Leu Asn Thr Leu Ile Pro Asn Gly Lys
65                  70                  75                  80

Ala Ile Ile Trp Asp Ser Arg Lys Gly Phe Ile Ile Ser Asn Ala Thr
                85                  90                  95

Tyr Lys Glu Ile Gly Leu Leu Thr Cys Glu Ala Thr Val Asn Gly His
            100                 105                 110

Leu Tyr Lys Thr Asn Tyr Leu Thr His Arg Gln Thr Asn Thr Ile Ile
        115                 120                 125

Asp Val Val Leu Ser Pro Ser His Gly Ile Glu Leu Ser Val Gly Glu
    130                 135                 140

Lys Leu Val Leu Asn Cys Thr Ala Arg Thr Glu Leu Asn Val Gly Ile
145                 150                 155                 160

Asp Phe Asn Trp Glu Tyr Pro Ser Ser Lys His Gln His Lys Lys Leu
                165                 170                 175

Val Asn Arg Asp Leu Lys Thr Gln Ser Gly Ser Glu Met Lys Lys Phe
            180                 185                 190

Leu Ser Thr Leu Thr Ile Asp Gly Val Thr Arg Ser Asp Gln Gly Leu
        195                 200                 205

Tyr Thr Cys Ala Ala Ser Ser Gly Leu Met Thr Lys Lys Asn Ser Thr
```

```
                  210                 215                 220
Phe Val Arg Val His Glu Lys Gly Pro Gly Ala Cys Gly Cys
225                 230                 235

<210> SEQ ID NO 21
<211> LENGTH: 240
<212> TYPE: PRT
<213> ORGANISM: homo sapiens

<400> SEQUENCE: 21

Met Val Ser Tyr Trp Asp Thr Gly Val Leu Leu Cys Ala Leu Leu Ser
1               5                   10                  15

Cys Leu Leu Leu Thr Gly Ser Ser Ser Gly Ser Asp Thr Gly Arg Pro
                20                  25                  30

Phe Val Glu Met Tyr Ser Glu Ile Pro Glu Ile Ile His Met Thr Glu
            35                  40                  45

Gly Arg Glu Leu Val Ile Pro Cys Arg Val Thr Ser Pro Asn Ile Thr
        50                  55                  60

Val Thr Leu Lys Lys Phe Pro Leu Asp Thr Leu Ile Pro Asp Gly Lys
65                  70                  75                  80

Arg Ile Ile Trp Asp Ser Arg Lys Gly Phe Ile Ile Ser Asn Ala Thr
                85                  90                  95

Tyr Lys Glu Ile Gly Leu Leu Thr Cys Glu Ala Thr Val Asn Gly His
            100                 105                 110

Leu Tyr Lys Thr Asn Tyr Leu Thr His Arg Gln Thr Asn Thr Ile Ile
        115                 120                 125

Asp Val Val Leu Ser Pro Ser His Gly Ile Glu Leu Ser Val Gly Glu
    130                 135                 140

Lys Leu Val Leu Asn Cys Thr Ala Arg Thr Glu Leu Asn Val Gly Ile
145                 150                 155                 160

Asp Phe Asn Trp Glu Tyr Pro Ser Ser Lys His Gln His Lys Lys Leu
                165                 170                 175

Val Asn Arg Asp Leu Lys Thr Gln Ser Gly Ser Glu Met Lys Lys Phe
            180                 185                 190

Leu Ser Thr Leu Thr Ile Asp Gly Val Thr Arg Ser Asp Gln Gly Leu
        195                 200                 205

Tyr Thr Cys Ala Ala Ser Ser Gly Leu Met Thr Lys Lys Asn Ser Thr
    210                 215                 220

Phe Val Arg Val His Glu Lys Asp Lys Thr His Thr Cys Pro Pro Cys
225                 230                 235                 240

<210> SEQ ID NO 22
<211> LENGTH: 240
<212> TYPE: PRT
<213> ORGANISM: homo sapiens

<400> SEQUENCE: 22

Met Val Ser Tyr Trp Asp Thr Gly Val Leu Leu Cys Ala Leu Leu Ser
1               5                   10                  15

Cys Leu Leu Leu Thr Gly Ser Ser Ser Gly Ser Asp Thr Gly Arg Pro
                20                  25                  30

Phe Val Glu Met Tyr Ser Glu Ile Pro Glu Ile Ile His Met Thr Glu
            35                  40                  45

Gly Arg Glu Leu Val Ile Pro Cys Arg Val Thr Ser Pro Asn Ile Thr
        50                  55                  60

Val Thr Leu Lys Lys Phe Pro Leu Asp Thr Leu Ile Pro Asp Gly Lys
```

```
                65                  70                  75                  80
Arg Ile Ile Trp Asp Ser Arg Lys Gly Phe Ile Ile Ser Asn Ala Thr
                85                  90                  95

Tyr Lys Glu Ile Gly Leu Leu Thr Cys Glu Ala Thr Val Asn Gly His
            100                 105                 110

Leu Tyr Lys Thr Asn Tyr Leu Thr His Arg Gln Thr Asn Thr Ile Ile
            115                 120                 125

Asp Val Val Leu Ser Pro Ser His Gly Ile Glu Leu Ser Val Gly Glu
        130                 135                 140

Lys Leu Val Leu Asn Cys Thr Ala Arg Thr Glu Leu Asn Val Gly Ile
145                 150                 155                 160

Asp Phe Asn Trp Glu Tyr Pro Ser Ser Lys His Gln His Lys Lys Leu
            165                 170                 175

Val Asn Arg Asp Leu Lys Thr Gln Ser Gly Ser Glu Met Lys Lys Phe
            180                 185                 190

Leu Ser Thr Leu Thr Ile Asp Gly Val Thr Arg Ser Asp Gln Gly Leu
            195                 200                 205

Tyr Thr Cys Ala Ala Ser Ser Gly Leu Met Thr Lys Lys Asn Ser Thr
        210                 215                 220

Phe Val Arg Val His Glu Lys Asp Lys Thr His Thr Ser Pro Pro Cys
225                 230                 235                 240

<210> SEQ ID NO 23
<211> LENGTH: 237
<212> TYPE: PRT
<213> ORGANISM: homo sapiens

<400> SEQUENCE: 23

Met Val Ser Tyr Trp Asp Thr Gly Val Leu Leu Cys Ala Leu Leu Ser
1               5                   10                  15

Cys Leu Leu Leu Thr Gly Ser Ser Ser Gly Ser Asp Thr Gly Arg Pro
            20                  25                  30

Phe Val Glu Met Tyr Ser Glu Ile Pro Glu Ile Ile His Met Thr Glu
        35                  40                  45

Gly Arg Glu Leu Val Ile Pro Cys Arg Val Thr Ser Pro Asn Ile Thr
    50                  55                  60

Val Thr Leu Lys Lys Phe Pro Leu Asp Thr Leu Ile Pro Asp Gly Lys
65                  70                  75                  80

Arg Ile Ile Trp Asp Ser Arg Lys Gly Phe Ile Ile Ser Asn Ala Thr
                85                  90                  95

Tyr Lys Glu Ile Gly Leu Leu Thr Cys Glu Ala Thr Val Asn Gly His
            100                 105                 110

Leu Tyr Lys Thr Asn Tyr Leu Thr His Arg Gln Thr Asn Thr Ile Ile
            115                 120                 125

Asp Val Val Leu Ser Pro Ser His Gly Ile Glu Leu Ser Val Gly Glu
        130                 135                 140

Lys Leu Val Leu Asn Cys Thr Ala Arg Thr Glu Leu Asn Val Gly Ile
145                 150                 155                 160

Asp Phe Asn Trp Glu Tyr Pro Ser Ser Lys His Gln His Lys Lys Leu
            165                 170                 175

Val Asn Arg Asp Leu Lys Thr Gln Ser Gly Ser Glu Met Lys Lys Phe
            180                 185                 190

Leu Ser Thr Leu Thr Ile Asp Gly Val Thr Arg Ser Asp Gln Gly Leu
            195                 200                 205
```

```
Tyr Thr Cys Ala Ala Ser Ser Gly Leu Met Thr Lys Lys Asn Ser Thr
            210                 215                 220

Phe Val Arg Val His Glu Lys Asp Lys Thr His Thr Cys
225                 230                 235

<210> SEQ ID NO 24
<211> LENGTH: 434
<212> TYPE: PRT
<213> ORGANISM: homo sapiens

<400> SEQUENCE: 24

Ser Asp Thr Gly Arg Pro Phe Val Glu Met Tyr Ser Glu Ile Pro Glu
  1               5                  10                  15

Ile Ile His Met Thr Glu Gly Arg Glu Leu Val Ile Pro Cys Arg Val
             20                  25                  30

Thr Ser Pro Asn Ile Thr Val Thr Leu Lys Lys Phe Pro Leu Asp Thr
         35                  40                  45

Leu Ile Pro Asp Gly Lys Arg Ile Ile Trp Asp Ser Arg Lys Gly Phe
 50                  55                  60

Ile Ile Ser Asn Ala Thr Tyr Lys Glu Ile Gly Leu Leu Thr Cys Glu
65                  70                  75                  80

Ala Thr Val Asn Gly His Leu Tyr Lys Thr Asn Tyr Leu Thr His Arg
                 85                  90                  95

Gln Thr Asn Thr Ile Ile Asp Val Val Leu Ser Pro Ser His Gly Ile
            100                 105                 110

Glu Leu Ser Val Gly Glu Lys Leu Val Leu Asn Cys Thr Ala Arg Thr
        115                 120                 125

Glu Leu Asn Val Gly Ile Asp Phe Asn Trp Glu Tyr Pro Ser Ser Lys
    130                 135                 140

His Gln His Lys Lys Leu Val Asn Arg Asp Leu Lys Thr Gln Ser Gly
145                 150                 155                 160

Ser Glu Met Lys Lys Phe Leu Ser Thr Leu Thr Ile Asp Gly Val Thr
                165                 170                 175

Arg Ser Asp Gln Gly Leu Tyr Thr Cys Ala Ala Ser Ser Gly Leu Met
            180                 185                 190

Thr Lys Lys Asn Ser Thr Phe Val Arg Val His Glu Lys Glu Ser Lys
        195                 200                 205

Tyr Gly Pro Pro Cys Pro Pro Cys Pro Ala Pro Glu Phe Leu Gly Gly
    210                 215                 220

Pro Ser Val Phe Leu Phe Pro Pro Lys Pro Lys Asp Thr Leu Met Ile
225                 230                 235                 240

Ser Arg Thr Pro Glu Val Thr Cys Val Val Val Asp Val Ser Gln Glu
                245                 250                 255

Asp Pro Glu Val Gln Phe Asn Trp Tyr Val Asp Gly Val Glu Val His
            260                 265                 270

Asn Ala Lys Thr Lys Pro Arg Glu Glu Gln Phe Asn Ser Thr Tyr Arg
        275                 280                 285

Val Val Ser Val Leu Thr Val Leu His Gln Asp Trp Leu Asn Gly Lys
    290                 295                 300

Glu Tyr Lys Cys Lys Val Ser Asn Lys Gly Leu Pro Ser Ser Ile Glu
305                 310                 315                 320

Lys Thr Ile Ser Lys Ala Lys Gly Gln Pro Arg Glu Pro Gln Val Tyr
                325                 330                 335

Thr Leu Pro Pro Ser Gln Glu Glu Met Thr Lys Asn Gln Val Ser Leu
            340                 345                 350
```

-continued

```
Thr Cys Leu Val Lys Gly Phe Tyr Pro Ser Asp Ile Ala Val Glu Trp
        355                 360                 365

Glu Ser Asn Gly Gln Pro Glu Asn Asn Tyr Lys Thr Thr Pro Pro Val
        370                 375                 380

Leu Asp Ser Asp Gly Ser Phe Phe Leu Tyr Ser Arg Leu Thr Val Asp
385                 390                 395                 400

Lys Ser Arg Trp Gln Glu Gly Asn Val Phe Ser Cys Ser Val Met His
                405                 410                 415

Glu Ala Leu His Asn His Tyr Thr Gln Lys Ser Leu Ser Leu Ser Leu
            420                 425                 430

Gly Lys
```

VEGF-BINDING FUSION PROTEINS AND NUCLEIC ACIDS ENCODING THE SAME

CROSS-REFERENCE TO RELATED APPLICATIONS

This application is a continuation-in-part of application Ser. Nos. 11/016,097 filed 17 Dec. 2004 and 11/016,503 filed 17 Dec. 2004, which are divisionals of Ser. No. 10/009,852 filed 6 Dec. 2001, now U.S. Pat No. 7,070,959, which is the National Stage of International Application No. PCT/US00/14142 filed 23 May 2000, which claims the benefit under 35 USC § 119(e) of U.S. provisional application No. 60/138,133 filed 8 Jun. 1999; and Application Ser. No. 10/880,021 filed 29 Jun. 2004, now U.S. Pat. No. 7,279,159 which is a continuation-in-part of Ser. No. 10/609,775 filed 30 Jun. 2003 now U.S. Pat. No. 7,087,411, which is a continuation-in-part of Ser. No. 10/009,852 filed 6 Dec. 2001, now U.S. Pat. No. 7,070,959, which is the National Stage of International Application No. PCT/US00/14142 filed 23 May 2000, which claims the benefit under 35 USC § 119(e) of U.S. provisional Application No. 60/138,133 filed 8 Jun. 1999, which applications are herein specifically incorporated by reference in their entireties.

BACKGROUND OF THE INVENTION

1. Field of the Invention

The invention encompasses fusion polypeptides capable of binding vascular endothelial cell growth factor (VEGF), VEGF family members, and splice variants with specifically desirable characteristics, as well as therapeutic methods of use.

2. Brief Summary of the Invention

In a first aspect, the invention features an isolated nucleic acid molecule encoding a fusion polypeptide comprising receptor components R1-R2-F, wherein R1 is vascular endothelial cell growth factor (VEGF) receptor component Ig domain 2 of Flt-1 (Flt1D2), R2 is VEGF receptor component Ig domain 3 of Flk-1 (Flk1D3) (also known as KDR), and F is a fusion component.

In a related second aspect, the invention features a VEGF-binding fusion polypeptide comprising VEGF receptor components R1-R2-F, wherein R1, R2, and F are as defined above. The components may be connected directly to each other or connected via one or more spacer sequences. In a preferred embodiment, R1 and R2 are the only receptor components present. In a specific embodiment, the VEGF-binding fusion polypeptide is amino acids 27-129 (R1) and 130-231 (R2) of SEQ ID NO:8, or a variant thereof.

The fusion component F is selected from the group consisting of a multimerizing component, a serum protein, or a molecule capable of binding a serum protein. In a preferred embodiment, F is a multimerizing component capable of interacting with a multimerizing component on another fusion polypeptide to form a multimeric structure, e.g., a dimer or trimer. Most preferably, the F is selected from the group consisting of (i) a multimerizing component comprising a cleavable region (C-region), (ii) a truncated multimerizing component, (iii) an amino acid sequence between 1 to about 200 amino acids in length having at least one cysteine residue, (iv) a leucine zipper, (v) a helix loop motif and (vi) a coil-coil motif. Preferably, the multimerizing component is an immunoglobulin domain. In one embodiment, F is a full-length or truncated immunoglobulin domain consisting of amino acids 232-458, 232-457, or 352-458 of SEQ ID NO:8.

The receptor components may be arranged in different orders, for example, R1R2F; R2R1F; R1FR2; R2FR1; FR1R2; FR2R1, etc. The components of the fusion polypeptide may be connected directly to each other, or connected via a spacer sequence.

In a third aspect, the invention features a multimeric VEGF-binding protein, comprising two or more fusion polypeptides of the invention (also called a VEGF "trap"). A VEGF trap composed of two fusion polypeptides having at least one truncated multimerizing component is termed a "truncated mini-trap." The multimeric VEGF-binding protein of the invention is capable of binding VEGF with an affinity (Kd) of at least $1\times10^{-10}$ M, preferably at least $1\times10^{-11}$ M, even more preferably at least $1\times10^{-12}$ M, as measured by BIACORE™ based assays.

The C-region may be created in the multimerizing component by insertion, deletion, or mutation, such that an enzymatically or chemically cleavable site is created. The C-region may be created in any multimerizing component and at any position within; preferably, the C-region is created in a full-length Fc domain, or a fragment thereof, or a $C_H3$ domain. The C-region may be a site cleavable by an enzyme, such as, thrombin, ficin, pepsin, matrilysin, or prolidase or cleavable chemically by, for example, formic acid or $CuCl_2$.

In all embodiments of the VEGF-binding fusion polypeptides of the invention (including full length VEGF-binding fusion polypeptides, truncated VEGF-binding fusion polypeptides, etc.), a signal sequence (S) may be included at the beginning (or N-terminus) of the fusion polypeptide of the invention. The signal sequence may be native to the cell, recombinant, or synthetic.

The components of the fusion polypeptide may be connected directly to each other or be connected via spacers. In specific embodiments, one or more receptor and/or fusion partner components of the fusion polypeptide are connected directly to each other without spacers. In other embodiments, one or more receptor and/or fusion partner components are connected with spacers.

In a fourth aspect, the invention encompasses vectors comprising the nucleic acid molecules of the invention, including expression vectors comprising the nucleic acid molecule operatively linked to an expression control sequence. In a fifth aspect, the invention encompasses host-vector systems for the production of a fusion polypeptide which comprise the expression vector, in a suitable host cell; host-vector systems wherein the suitable host cell is a bacterial, yeast, insect, mammalian cell; an *E. Coli* cell, or a COS or CHO cell. Additional encompassed in a sixth aspect are VEGF-binding fusion polypeptides of the invention modified by acetylation or pegylation, and other post-translational modifications resulting from expression in a mammalian cell line. Methods for acetylating or pegylating a protein are well known in the art. In specific embodiments, the fusion polypeptide of the invention expressed in a mammalian cell line such as a CHO cell comprises amino acids 27-457 of SEQ ID NO:8 and is glycosylated at Asn residues 62, 94, 149, 222 and 308.

In a related seventh aspect, the invention features a method of producing a VEGF-binding fusion polypeptides of the invention, comprising culturing a host cell transfected with a vector comprising a nucleic acid sequence of the invention, under conditions suitable for expression of the protein from the host cell, and recovering the fusion polypeptides so produced.

The VEGF-binding fusion polypeptides of the invention are therapeutically useful for treating any disease or condition which is improved, ameliorated, or inhibited by removal, inhibition, or reduction of VEGF. A non-exhaustive list of specific conditions improved by inhibition or reduction of VEGF include, for example, undesirable plasma leakage or vascular permeability, undesirable blood vessel growth, e.g., such as in a tumor, edema associated with inflammatory disorders such as psoriasis or arthritis, including rheumatoid arthritis; asthma; generalized edema associated with burns; ascites and pleural effusion associated with tumors, inflammation or trauma; chronic airway inflammation; asthma; capillary leak syndrome; sepsis; kidney disease associated with increased leakage of protein; pancreatic ductal adenocarcinoma (PDAC) and eye disorders such as age related macular degeneration and diabetic retinopathy. The VEGF mini-trap is particularly useful in treatment of eye disorders, and as an adjuvant to eye surgeries, including glaucoma surgery; and the treatment of intra-ocular tumors, such as for example, uveal melanoma, retinoblastoma, via intravitreal delivery.

Accordingly, in an eighth aspect, the invention features a therapeutic method for the treatment of a VEGF-related disease or condition, comprising administering a VEGF-binding fusion polypeptide of the invention to a subject suffering from a VEGF-related disease or condition. Although any mammal can be treated by the therapeutic methods of the invention, the subject is preferably a human patient suffering from or at risk of suffering from a condition or disease which can be improved, ameliorated, inhibited or treated with a VEGF-binding fusion polypeptide of the invention.

In a ninth aspect, the invention features pharmaceutical compositions comprising a VEGF-binding fusion polypeptide of the invention with a pharmaceutically acceptable carrier. Such pharmaceutical compositions may comprise a dimeric fusion polypeptide trap, or nucleic acids encoding the fusion polypeptide. The mini-traps of the invention find specific uses in conditions in which a VEGF inhibitor with reduced serum half life (e.g., faster clearance), and/or increased tissue penetration due to smaller size is desirable. Specific applications for the VEGF mini-trap include, for example, diseases where local administration to a specific tissue or cell is desirable. Examples of such a condition or disease are ocular diseases of the eye.

Other objects and advantages will become apparent from a review of the ensuing detailed description.

BRIEF DESCRIPTION OF THE FIGURES

FIGS. 1A-C provides sugar chain mass assignment for the oligosaccharides of two batches of VEGF trap protein (SEQ ID NO:8) (P3=VGT C04003M500; P3.5=C04008M500).

DETAILED DESCRIPTION OF THE INVENTION

Figure 1B:
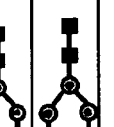
Figure 1B:
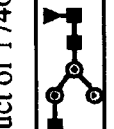
Figure 1B:
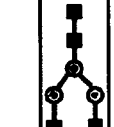
Figure 1B:
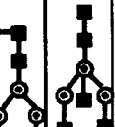
Figure 1B:
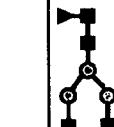
Figure 1B:
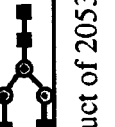
Figure 1B:
Figure 1B:

Before the present methods are described, it is to be understood that this invention is not limited to particular methods, and experimental conditions described, as such methods and conditions may vary. It is also to be understood that the terminology used herein is for the purpose of describing particular embodiments only, and is not intended to be limiting, since the scope of the present invention will be limited only the appended claims.

As used in this specification and the appended claims, the singular forms "a", "an", and "the" include plural references unless the context clearly dictates otherwise. Thus for example, a reference to "a method" includes one or more methods, and/or steps of the type described herein and/or which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to describe the methods and/or materials in connection with which the publications are cited.

General Description

The invention encompasses multimeric VEGF-binding proteins capable of binding and inhibiting VEGF activity with a Kd of at least $x \times 10^{-10}$ M. The molecules of the invention bind and inhibit the biological action of VEGF and/or the physiological reaction or response. For a description of VEGF-receptor-based antagonist VEGF traps Flt1D2.Flk1D3.FcΔC1(a) (SEQ ID NOs:5-6) and VEGFR1R2-FcΔC1(a) (SEQ ID NOs:7-8), see PCT WO/0075319, the contents of which is incorporated in its entirety herein by reference.

Nucleic Acid Constructs and Expression

The present invention provides for the construction of nucleic acid molecules encoding fusion polypeptides capable of multimerizing to form VEGF traps capable of binding VEGF with high affinity. The nucleic acid molecules of the invention may encode wild-type R1 and R2 receptor components, or may encode functionally equivalent variants thereof. Amino acid sequence variants of the R1 and R2 receptor components of the traps of the invention may also be prepared by creating mutations in the encoding nucleic acid molecules. Such variants include, for example, deletions from, or insertions or substitutions of, amino acid residues within the amino acid sequence of R1 and R2. Any combination of deletion, insertion, and substitution may be made to arrive at a final construct, provided that the final construct possesses the ability to bind and inhibit VEGF.

These nucleic acid molecules are inserted into a vector that is able to express the fusion polypeptides when introduced into an appropriate host cell. Appropriate host cells include, but are not limited to, bacterial, yeast, insect, and mammalian cells. Any of the methods known to one skilled in the art for the insertion of DNA fragments into a vector may be used to construct expression vectors encoding the fusion polypeptides of the invention under control of transcriptional/translational control signals.

Expression of the nucleic acid molecules of the invention may be regulated by a second nucleic acid sequence so that the molecule is expressed in a host transformed with the recombinant DNA molecule. For example, expression may be controlled by any promoter/enhancer element known in the art. Promoters which may be used to control expression of the chimeric polypeptide molecules include, but are not limited to, a long terminal repeat (Squinto et al. (1991) Cell 65:1-20); SV40 early promoter region, CMV, M-MuLV, thymidine kinase promoter, the regulatory sequences of the metallothionine gene; prokaryotic expression vectors such as the β-lactamase promoter, or the tac promoter (see also Scientific American (1980) 242:74-94); promoter elements from yeast or other fungi such as Gal 4 promoter, ADH, PGK, alkaline phosphatase, and tissue-specific transcriptional control regions derived from genes such as elastase I.

Expression vectors capable of being replicated in a bacterial or eukaryotic host comprising the nucleic acid molecules of the invention are used to transfect the host and thereby direct expression of such nucleic acids to produce the fusion polypeptides of the invention, which form traps capable of binding to VEGF. Transfected cells may transiently or, preferably, constitutively and permanently express the VEGF traps of the invention.

The fusion polypeptides of the invention may be purified by any technique which allows for the subsequent formation of a stable, biologically active trap. For example, and not by way of limitation, the factors may be recovered from cells either as soluble proteins or as inclusion bodies, from which they may be extracted quantitatively by 8M guanidinium hydrochloride and dialysis (see, for example, U.S. Pat. No. 5,663,304). In order to further purify the factors, conventional ion exchange chromatography, hydrophobic interaction chromatography, reverse phase chromatography or gel filtration may be used.

VEGF Receptor Components

The VEGF receptor components of the VEGF mini trap consist of the Ig domain 2 of Flt-1 (Flt1D2) (R1), the Ig domain 3 of Flk-1 (Flk1D3) (R2) (together, R1R2. The term "Ig domain" of Flt-1 or Flk-1 is intended to encompass not only the complete wild-type domain, but also insertional, deletional, and/or substitutional variants thereof which substantially retain the functional characteristics of the intact domain. It will be readily apparent to one of skill in the art that numerous variants of the above Ig domains can be obtained which will retains substantially the same functional characteristics as the wild-type domain.

The term "functional equivalents" when used in reference to R1 and R2, is intended to encompass an R1 and R2 domain with at least one alteration, e.g., a deletion, addition, and/or substitution, which retains substantially the same functional characteristics as does the wild type R1 and R2, that is, a substantially equivalent binding to VEGF. It will be appreciated that various amino acid substitutions can be made in R1 and R2 without departing from the spirit of the invention with respect to the ability of these receptor components to bind and inactivate VEGF. The functional characteristics of the traps of the invention may be determined by any suitable screening assay known to the art for measuring the desired characteristic. Examples of such assays are described in the experimental section below which allow determination of binding affinity of the traps for VEGF (Kd), as well as their half-life of dissociation of the trap-ligand complex ($T_{1/2}$). Other assays, for example, a change in the ability to specifically bind to VEGF can be measured by a competition-type VEGF binding assay. Modifications of protein properties such as thermal stability, hydrophobicity, susceptibility to proteolytic degradation, or tendency to aggregate may be measured by methods known to those of skill in the art.

The components of the fusion polypeptide may be connected directly to each other or be connected via spacers. Generally, the term "spacer" (or linker) means one or more molecules, e.g., nucleic acids or amino acids, or non-peptide moieties, such as polyethylene glycol, which may be inserted between one or more component domains. For example, spacer sequences may be used to provide a desirable site of interest between components for ease of manipulation. A spacer may also be provided to enhance expression of the fusion polypeptide from a host cell, to decrease steric hindrance such that the component may assume its optimal tertiary structure and/or interact appropriately with its target molecule. For spacers and methods of identifying desirable spacers, see, for example, George et al. (2003) Protein Engineering 15:871-879, herein specifically incorporated by reference. A spacer sequence may include one or more amino acids naturally connected to a receptor component, or may be an added sequence used to enhance expression of the fusion polypeptides, provide specifically desired sites of interest, allow component domains to form optimal tertiary structures and/or to enhance the interaction of a component with its target molecule. In one embodiment, the spacer comprises one or more peptide sequences between one or more components which is (are) between 1-100 amino acids, preferably 1-25.

In the most specific embodiments, R1 is amino acids 27-126 of SEQ ID NO:6, or 1-126 of SEQ ID NO:6 (including the signal sequence 1-26); or amino acids 27-129 of SEQ ID NO:8, or 1-129 of SEQ ID NO:8 (including the signal sequence at 1-26). In the most specific embodiments, R2 is amino acids 127-228 of SEQ ID NO:6, or amino acids 130-231 of SEQ ID NO:8. When, for example, R2 is placed at the N-terminus of the fusion polypeptide, a signal sequence may desirably precede the receptor component. The receptor component(s) attached to the multimerizing component may further comprise a spacer component, for example, the GPG sequence of amino acids 229-231 of SEQ ID NO:5.

Fusion and Multimerizing Components

The fusion partner is any component that enhances the functionality of the fusion polypeptide. Thus, for example, an fusion partner may enhance the biological activity of the fusion polypeptide, aid in its production and/or recovery, or enhance a pharmacological property or the pharmacokinetic profile of the fusion polypeptide by, for example, enhancing its serum half-life, tissue penetrability, lack of immungenicity, or stability. In preferred embodiments, the fusion partner is selected from the group consisting of a multimerizing component, a serum protein, or a molecule capable of binding a serum protein.

When the fusion partner is a serum protein or fragment thereof, it is selected from the group consisting of α-1-microglobulin, AGP-1, orosomuciod, α-1-acid glycoprotein, vitamin D binding protein (DBP), hemopexin, human serum albumin (hSA), transferrin, ferritin, afamin, haptoglobin, α-fetoprotein thyroglobulin, α-2-HS-glycoprotein, β-2-glycoprotein, hyaluronan-binding protein, syntaxin, C1R, C1q a chain, galectin3-Mac2 binding protein, fibrinogen, polymeric Ig receptor (PIGR), α-2-macroglobulin, urea transport protein, haptoglobin, IGFBPs, macrophage scavenger receptors, fibronectin, giantin, Fc, α-1-antichyromotrypsin, α-1-antitrypsin, antithrombin III, apolipoprotein A-I, apolipoprotein B, β-2-microglobulin, ceruloplasmin, complement component C3 or C4, CI esterase inhibitor, C-reactive protein, cystatin C, and protein C. In a more specific embodiment, fusion partner is selected from the group consisting of α-1-microglobulin, AGP-1, orosomuciod, α-1-acid glycoprotein, vitamin D binding protein (DBP), hemopexin, human serum albumin (hSA), afamin, and haptoglobin. The inclusion of a fusion partner component may extend the serum half-life of the fusion polypeptide of the invention when desired. See, for example, U.S. Pat. Nos. 6,423,512, 5,876,969, 6,593,295, and 6,548,653, herein specifically incorporated by reference in their entirety, for examples of serum albumin fusion polypeptides. hSA is widely distributed throughout the body, particularly in the intestinal and blood components, and has an important role in the maintenance of osmolarity and plasma volume. It is slowly cleared in the liver, and typically has an in vivo half-life of 14-20 days in humans (Waldmann et al. (1977) Albumin, Structure Function and Uses; Pergamon Press; pp. 255-275).

When a fusion partner is a molecule capable of binding a serum protein, the molecule may be a synthetic small molecule, a lipid or liposome, a nucleic acid, including a synthetic nucleic acid such as an aptomer, a peptide, or an oligosaccharide. The molecule may further be a protein, such as, for example, FcγR1, FcγR2, FcγR3, polymeric Ig receptor (PIGR), ScFv, and other antibody fragments specific for a serum protein.

When the fusion partner is a multimerizing component (MC), it is any natural or synthetic sequence capable of interacting with another MC to form a higher order structure, e.g., a dimer, a trimer, etc. Suitable MCs may include a leucine zipper, including leucine zipper domains derived from c-jun or c-fos; sequences derived from the constant regions of kappa or lambda light chains; synthetic sequences such as helix-loop-helix motifs (Müller et al. (1998) FEBS Lett. 432: 45-49), coil-coil motifs, etc., or other generally accepted multimerizing domains known to the art. In some embodiments, the fusion component comprises an immunoglobulin-derived domain from, for example, human IgG, IgM or IgA. In specific embodiments, the immunoglobulin-derived domain may be selected from the group consisting of the Fc domain of IgG, the heavy chain of IgG, and the light chain of IgG. The Fc domain of IgG may be selected from the isotypes IgG1, IgG2, IgG3, and IgG4, as well as any allotype within each isotype group. In one example of the VEGF trap of the invention, the multimerizing component is an IgG4 Fc domain (SEQ ID NO:24).

The fusion polypeptides of the invention may comprise a truncated multimerizing component. For example, when the multimerizing component is a human Fc, in a particular embodiment the $C_H2$ component of Fc may be deleted (239-351 of SEQ ID NO:8) (Larson et al. 2005 J Mol Biol 348: 1177-90, which publication is herein specifically incorporated by reference in its entirety).

In specific embodiments, the Fc from IgG1 may be modified to reduce effector functions. For example, the Fc may replace Asn297 (using cabot numbering) with a different amino acid, for example, Ala or Gln, Asp, Met, or Tyr, to eliminate glycosylation (Tao et al. 1989 J. Immunol 143: 2595-2601, which publication is herein specifically incorporated by reference in its entirety). Glycosylation may also be modified using mutant CHO cell lines, which either eliminate glycosylation or modify the extent of glycosylation (Wright et al. 1998 J. Immunol. 160:3393-3402, which publication is herein specifically incorporated by reference in its entirety). Mutations known by the art to eliminate effector functions are Leu234Ala, Leu235Ala/Glu (U.S. patent publication 2005/0100965; Reddy et al. 2000 J. Immunol. 164:1925-1933, which publications are herein specifically incorporated by reference in their entirety), and the class 1 mutations described in Sheilds et al 2001 JBC 276:6591-6604, which publication is herein specifically incorporated by reference in its entirety), such as Arg265Ala and Phe329Ala. An IgG4 or IgG2 Fc can also be used to reduce effector functions. In the case of IgG4, mutations that stabilize the molecule may be desirable, for example, Ser228Pro to stabilize covalent dimer formation (1993 Mol. Immunol. 30:105-108, which publication is herein specifically incorporated by reference in its entirety). Alternatively, the molecule may be enhanced for effector function activity by including mutations such as Ser298Ala, Glu33Ala, Lys334Ala (Sheilds et al supra; U.S. 2005/0054832, which publication is herein specifically incorporated by reference in its entirety, or by decreasing the fucosylation of the sugar side chain (Niwa et al. 2005 Clin Cancer Res 11:2327-2336, which publication is herein specifically incorporated by reference in its entirety).

The in vivo half-life of the antibodies can also be improved by modifying the salvage receptor epitope of the Ig constant domain or an Ig-like constant domain such that the molecule does not comprise an intact CH2 domain (239-351) or an intact Ig Fc region (U.S. Pat. No. 6,121,022; U.S. Pat. No. 6,194,551, which publications are herein specifically incorporated by reference in their entirety). The in vivo half-life can furthermore be increased by making mutations in the Fc region, e.g. by substituting Thr at Leu252, Thr at Ser254, or Thr at Phe256 (U.S. Pat. No. 6,277,375, which publication is herein specifically incorporated by reference in its entirety).

Therapetic Uses

The VEGF-binding traps of the invention are therapeutically useful for treating any disease or condition which is improved, ameliorated, inhibited or prevented by removal, inhibition, or reduction of VEGF. A non-exhaustive list of specific conditions improved by inhibition or reduction of VEGF include, clinical conditions that are characterized by excessive vascular endothelial cell proliferation, vascular permeability, edema or inflammation such as brain edema associated with injury, stroke or tumor; edema associated with inflammatory disorders such as psoriasis or arthritis, including rheumatoid arthritis; asthma; generalized edema associated with burns; ascites and pleural effusion associated with tumors, inflammation or trauma; chronic airway inflammation; capillary leak syndrome; sepsis; kidney disease associated with increased leakage of protein; and eye disorders such as age related macular degeneration and diabetic retinopathy.

The compositions of the invention are therapeutically useful for treating a wide variety of diseases associated with increased VEGF levels. For example, exaggerated Th2 inflammation and airway remodeling are characteristic in the pathogenesis of asthma (see, for example, Elias et al. (1999) J. Clin. Invest. 104:1001-6). Elevated VEGF levels have been detected in tissues and biologic samples from patients with asthma, which correlate directly with disease activity (Lee et al. (2001) J. Allergy Clin. Immunol. 107:1106-1108) and inversely with airway caliber and airway responsiveness. Further, VEGF has been postulated to contribute to asthmatic tissue edema.

Another disease associated with increased VEGF is pancreatic ductal adenocarcinoma (PDAC). This malignancy often exhibits enhanced foci of endothelial cell proliferation and frequently overexpresses VEGF (Ferrara (1999) J. Mol. Med. 77:527-543). PDAC is responsible for over 20% of deaths due to gastrointestinal malignancies, making it the fourth most common cause of cancer-related mortality in the U.S. and other industrialized countries. Experimental evidence supports an important role for VEGF in pancreatic cancer, thus a VEGF inhibitor has promise as a therapeutic to attenuate intrapancreatic tumor growth and regional and distal metastasis.

A smaller, non-glycosylated mini-trap expressed in *E. coli* (Example 4), a glycosylated mini-trap expressed in CHO cells (Example 5), or a receptor-based monomeric trap (Example 6) has optimized characteristics for local/intra-vitreal delivery, ie. a shorter serum half life for faster clearance and minimizing unwanted systemic exposure. In addition due to its smaller size, the mini-trap has the ability to penetrate through the inner-limiting membrane (ILM) in the eye, and diffuse through the vitreous to the retina/retinal pigment epithelial (RPE) layer which will help to treat retinal disease. Additionally, the mini-trap can be used for local administration for the treatment of ocular disease such as choroidal neovascularization, diabetic macular edema, proliferative diabetic retinopathy, corneal neovascularization/transplant rejection. Still further, the mini-trap can be used in any situation where transient (short-term) blocking of VEGF is required, e.g., to avoid chronic exposure to VEGF blockade, such as, for example, in the treatment of psoriasis.

A serious problem leading to failure following glaucoma surgery is early inflammation and angiogenesis, as well as too aggressive wound healing. Accordingly, the VEGF traps of the invention may be usefully employed is as an adjuvant to glaucoma surgery to prevent early hem- and lymphangiogenesis and macrophage recruitement to the filterig bleb after glaucoma surgery, and improve surgical outcome.

Combination Therapies

In numerous embodiments, a VEGF trap may be administered in combination with one or more additional compounds or therapies, including a second VEGF trap molecule, a chemotherapeutic agent, surgery, catheter devices, and radiation. Combination therapy includes administration of a single pharmaceutical dosage formulation which contains a VEGF trap and one or more additional agents; as well as administration of a VEGF trap and one or more additional agent(s) in its own separate pharmaceutical dosage formulation. For example, a VEGF trap and a cytotoxic agent, a chemotherapeutic agent or a growth inhibitory agent can be administered to the patient together in a single dosage composition such as a combined formulation, or each agent can be administered in a separate dosage formulation. Where separate dosage formulations are used, the VEGF-specific fusion polypeptide of the invention and one or more additional agents can be administered concurrently, or at separately staggered times, i.e., sequentially.

The term "cytotoxic agent" as used herein refers to a substance that inhibits or prevents the function of cells and/or causes destruction of cells. The term is intended to include radioactive isotopes (e.g. $I^{131}$, $I^{125}$, $Y^{90}$ and $Re^{186}$), chemotherapeutic agents, and toxins such as enzymatically active toxins of bacterial, fungal, plant or animal origin, or fragments thereof.

A "chemotherapeutic agent" is a chemical compound useful in the treatment of cancer. Examples of chemotherapeutic agents include alkylating agents such as thiotepa and cyclosphosphamide (CYTOXAN®); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin carabicin, carminomycin, carzinophilin, chromomycins, dactinomycin, daunorubicin, detorubicin 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elfornithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofiran; spirogermanium tenuazonic acid; triaziquone; 2, 2', 2"-trichlorotriethylamine; urethan; vindesine; dacarbazine; mannoniustine; mitobronitol; mitolactol; pipobroman; gacytosine; arabinoside ("Ara-C"); cyclophosphamide; thiotepa; taxanes, e.g. paclitaxel (TAXOL®, Bristol-Myers Squibb Oncology, Princeton, N.J.) and docetaxel (TAXOTERE®; Aventis Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylornithine (DMFO); retinoic acid; esperamicins; capecitabine; and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY 117018, onapristone, and toremifene (FARESTON®); and anti-androgens such as flutamide, nilutamide, bicalutamide, leuprolide, and goserelin; and pharmaceutically acceptable salts, acids or derivatives of any of the above.

A "growth inhibitory agent" when used herein refers to a compound or composition which inhibits growth of a cell, especially a cancer cell either in vitro or in vivo. Examples of growth inhibitory agents include agents that block cell cycle progression (at a place other than S phase), such as agents that induce G1 arrest and M-phase arrest. Classical M-phase blockers include the vincas (vincristine and vinbiastine), TAXOL®, and topo II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C.

Methods of Administration

The invention provides methods of treatment comprising administering to a subject an effective amount of a VEGF trap of the invention. In a preferred aspect, the trap is substantially purified (e.g., substantially free from substances that limit its effect or produce undesired side-effects). The subject is preferably a mammal, and most preferably a human.

Various delivery systems are known and can be used to administer an agent of the invention, e.g., encapsulation in liposomes, microparticles, microcapsules, recombinant cells capable of expressing the compound, receptor-mediated endocytosis (see, e.g., Wu and Wu, 1987, J. Biol. Chem. 262:4429-4432), construction of a nucleic acid as part of a retroviral or other vector, etc. Methods of introduction can be enteral or parenteral and include but are not limited to intradermal, intramuscular, intraperitoneal, intravenous, subcutaneous, intranasal, intraocular, and oral routes. The compounds may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. Administration can be acute or chronic (e.g. daily, weekly, monthly, etc.) or in combination with other agents. Pulmonary administration can also be employed, e.g., by use of an inhaler or nebulizer, and formulation with an aerosolizing agent.

In another embodiment, the active agent can be delivered in a vesicle, in particular a liposome, in a controlled release system, or in a pump. In another embodiment where the active agent of the invention is a nucleic acid encoding a protein, the nucleic acid can be administered in vivo to promote expression of its encoded protein, by constructing it as part of an appropriate nucleic acid expression vector and administering it so that it becomes intracellular, e.g., by use of a retroviral vector (see, for example, U.S. Pat. No. 4,980,286), by direct injection, or by use of microparticle bombardment, or coating with lipids or cell-surface receptors or transfecting agents, or by administering it in linkage to a homeobox-like peptide which is known to enter the nucleus (see e.g., Joliot et al., 1991, Proc. Natl. Acad. Sci. USA 88:1864-1868), etc. Alternatively, a nucleic acid can be introduced intracellularly and incorporated within host cell DNA for expression, by homologous recombination.

In a specific embodiment, it may be desirable to administer the pharmaceutical compositions of the invention locally to the area in need of treatment; this may be achieved, for example, and not by way of limitation, by local infusion during surgery, topical application, e.g., by injection, by means of a catheter, or by means of an implant, the implant being of a porous, non-porous, or gelatinous material, including membranes, such as sialastic membranes, fibers, or commercial skin substitutes.

A composition useful in practicing the methods of the invention may be a liquid comprising an agent of the invention in solution, in suspension, or both. The term "solution/suspension" refers to a liquid composition where a first portion of the active agent is present in solution and a second portion of the active agent is present in particulate form, in suspension in a liquid matrix. A liquid composition also includes a gel. The liquid composition may be aqueous or in the form of an ointment. Further, the composition can take the form of a solid article that can be inserted in the eye, such as for example between the eye and eyelid or in the conjunctival sac, where the VEGF trap is released. Release from such an article is usually to the cornea, either via the lacrimal fluid, or directly to the cornea itself, with which the solid article is generally in direct contact. Solid articles suitable for implantation in the eye are generally composed primarily of bioerodible or nonbioerodible polymers. An aqueous solution and/or suspension can be in the form of eye drops. A desired dosage of the active agent can be measured by administration of a known number of drops into the eye. For example, for a drop volume of 25 µl, administration of 1-6 drops will deliver 25-150 µl of the composition.

An aqueous suspension or solution/suspension useful for practicing the methods of the invention may contain one or more polymers as suspending agents. Useful polymers include water-soluble polymers such as cellulosic polymers and water-insoluble polymers such as cross-linked carboxyl-containing polymers. An aqueous suspension or solution/suspension of the present invention is preferably viscous or muco-adhesive, or even more preferably, both viscous or mucoadhesive.

In another embodiment, the composition useful in practicing the methods of the invention is an in situ gellable aqueous composition. Such a composition comprises a gelling agent in a concentration effective to promote gelling upon contact with the eye or with lacrimal fluid. Suitable gelling agents include but are not limited to thermosetting polymers. The term "in situ gellable" as used herein is includes not only liquids of low viscosity that form gels upon contact with the eye or with lacrimal fluid, but also includes more viscous liquids such as semi-fluid and thixotropic gels that exhibit substantially increased viscosity or gel stiffness upon administration to the eye.

Pharmaceutical Compositions

The present invention also provides pharmaceutical compositions comprising a VEGF mini-trap of the invention. Such compositions comprise a therapeutically effective amount of one or more mini-traps, and a pharmaceutically acceptable carrier. The term "pharmaceutically acceptable" means approved by a regulatory agency of the Federal or a state government or listed in the U.S. Pharmacopeia or other generally recognized pharmacopeia for use in animals, and more particularly, in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. Examples of suitable pharmaceutical carriers are described in "Remington's Pharmaceutical Sciences" by E. W. Martin.

The VEGF mini-trap of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

Further more, aqueous compositions useful for practicing the methods of the invention have ophthalmically compatible pH and osmolality. One or more ophthalmically acceptable pH adjusting agents and/or buffering agents can be included in a composition of the invention, including acids such as acetic, boric, citric, lactic, phosphoric and hydrochloric acids; bases such as sodium hydroxide, sodium phosphate, sodium borate, sodium citrate, sodium acetate, and sodium lactate; and buffers such as citrate/dextrose, sodium bicarbonate and ammonium chloride. Such acids, bases, and buffers are included in an amount required to maintain pH of the composition in an ophthalmically acceptable range. One or more ophthalmically acceptable salts can be included in the composition in an amount sufficient to bring osmolality of the composition into an ophthalmically acceptable range. Such salts include those having sodium, potassium or ammonium cations and chloride, citrate, ascorbate, borate, phosphate, bicarbonate, sulfate, thiosulfate or bisulfite anions.

The amount of the trap that will be effective for its intended therapeutic use can be determined by standard clinical techniques based on the present description. In addition, in vitro assays may optionally be employed to help identify optimal dosage ranges. Generally, suitable dosage ranges for intravenous administration are generally about 50-5000 micrograms of active compound per kilogram body weight. Suitable dosage ranges for intranasal administration are generally about 0.01 pg/kg body weight to 1 mg/kg body weight. Effective doses may be extrapolated from dose-response curves derived from in vitro or animal model test systems.

For systemic administration, a therapeutically effective dose can be estimated initially from in vitro assays. For example, a dose can be formulated in animal models to achieve a circulating concentration range that includes the $IC_{50}$ as determined in cell culture. Such information can be used to more accurately determine useful doses in humans. Initial dosages can also be estimated from in vivo data, e.g., animal models, using techniques that are well known in the art. One having ordinary skill in the art could readily optimize administration to humans based on animal data.

Dosage amount and interval may be adjusted individually to provide plasma levels of the compounds that are sufficient to maintain therapeutic effect. In cases of local administration or selective uptake, the effective local concentration of the compounds may not be related to plasma concentration. One having skill in the art will be able to optimize therapeutically effective local dosages without undue experimentation.

The amount of compound administered will, of course, be dependent on the subject being treated, on the subject's weight, the severity of the affliction, the manner of administration, and the judgment of the prescribing physician. The therapy may be repeated intermittently while symptoms are detectable or even when they are not detectable. The therapy may be provided alone or in combination with other drugs.

Specific Embodiments

In the experiments described below, smaller VEGF traps were generated and their ability to bind VEGF was investigated. Such mini-traps are preferably uses in specific applications. For example, certain conditions or diseases may be preferably treated with local administration of a VEGF trap to a specific organ, tissue, or cell, rather than by systemic administration. In one exemplification of the mini-traps of the invention, a smaller VEGF trap was generated by directed cleavage of a dimerized VEGF trap having a cleavage region (C-region) generated in a Fc domain (Example 2). The truncated trap exhibited comparable affinity for VEGF and half-life as the full-sized parent trap. Examples 3-5 describe construction of fusion polypeptides having a VEGF receptor component and a multimerizing component consisting of one or two cysteine residues. Affinity measurements showed that the non-glycosylated fusion polypeptides expressed in *E. coli* or the glycosylated polypeptides expressed in CHO cells had comparable binding affinity for VEGF as the full-sized parent trap. Example 6 further illustrates a monomeric VEGF trap consisting of $(R1R2)_2$ which is capable of binding and inhibiting VEGF. Example 7 describes the construction of a VEGF mini-trap (SEQ ID NO:21) exhibiting high affinity binding for VEGF comparable to the full length trap (SEQ ID NO:8).

Proteins expressed in mammalian cell lines may contain multiple chemical modifications. Generally, these modifications of immunoglobulin proteins include removal of the signal peptide, truncation of the C-terminal lysine of the heavy chain (Lazar et al. (2004) Rapid Comm Mass Spec 18:239-244, which publication is herein specifically incorporated by reference in its entirety), and glycosylation. As described in Example 8, fusion polypeptides expressed in CHO cells were analyzed further to determine glycosylation patterns and oligosaccharide content. The fusion proteins were determined to comprise amino acids 28-457 of SEQ ID NO:8 and to be glycosylated at the Asn residues of positions 62, 94, 149, 222, and 308.

Other features of the invention will become apparent in the course of the following descriptions of exemplary embodiments which are given for illustration of the invention and are not intended to be limiting thereof.

EXAMPLES

The following example is put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1

Construction of Flt1D2.Flk1D3.FcΔC1(a)

The construction of a parent VEGF trap, Flt1D2.Flk1 D3.FcΔC1(a) (SEQ ID NOs:5-6), VEGFR1R2.FcΔC1(a) (SEQ ID NOs:7-8), and Flt1D2.VEGFRD3.FcΔC1 (a) (SEQ ID NOs:9-10) is described in detail in PCT publication WO/0075319, herein specifically incorporated by reference in its entirety. Also described in WO/0075319 are methods of constructing and expressing nucleic acid constructs encoding VEGF traps, methods of detecting and measuring VEGF trap binding to VEGF, methods of determining the stoichiometry of VEGF binding by BIACORE™ analysis, and pharmacokinetic analyses.

Example 2

Thrombin-Cleaved Dimeric VEGF Mini-Trap

The VEGFR1R2.FcΔC1(a) (SEQ ID NOs:7-8) construct was modified by insertion of a thrombin cleavage following the CPPC (SEQ ID NO:1) of the Fc domain. Purified VEGF trap (5 μg) was incubated with thrombin (Novagen) in 20 mM Tris-HCl, pH 8.4, 50 mM NaCl, 2.5 mM $CaCl_2$ for 16 hrs at 37° C. Controls included cleavage control protein (CCP) and parent VEGF trap protein incubated without thrombin. SDS-PAGE analysis (Tris-Glycine 4-20% gel; 5 μg protein per lane) verified correct cleavage (results not shown).

Affinity determination. The Kd of binding of each VEGF trap to hVEGF165 was determined as described in WO/0075319, for the parent VEGF trap, uncleaved VEGF trap containing a thrombin cleavage site ("uncleaved VEGF trap"), cleaved VEOF mini-trap and recombinant monomeric R1R2-myc myc his. Generally, the VEGF trap proteins were tested in a BIACORE™-based assay to evaluate their ability to bind to the Flt1 ligand, VEGF. in this assay, a VEGF trap protein was immobilized on the surface of a BIACORE™ chip (see BIACORE™ Instruction Manual, Pharmacia, Inc., Piscataway, N.J., for standard procedures) and a sample of hVEGF165 was passed over the coated chip. More specifically, the ability of the traps to block $VEGF_{165}$-dependent receptor phosphorylation was determined using primary human endothelial cells (HUVECs). $VEGF_{165}$ was incubated in the presence of varying concentrations of the test traps, and the mixture was added to HUVECs to stimulate tyrosine phosphorylation of VEGFR2. At sub-stoichiometric concentrations of VEGF trap, unbound VEGF induced receptor phosphorylation. However, at a 1:1 molar ratio of greater of a VEGF trap to ligand, complete blocking of receptor signaling was observed, establishing that a single molecule of a trap dimer is capable of blocking a single molecule of human VEGF$_{165}$. Thus, the high binding affinity of the VEGF trap for VEGF results in formation of a complex that prevents VEGF from interaction with cell surface receptors. Equivalent results were obtained for identical phosphorylation inhibition experiments for the parent VEGF trap, uncleaved VEGF trap, and cleaved VEGF mini-trap The results are shown in Table 1.

TABLE 1

| Trap | Kinetic Dissociation Rate (1/s) | $T_{1/2}$ (hr) |
| --- | --- | --- |
| parent VEGF trap | $5.51 \times 10^{-5} \pm 0.94\%$ | 3.5 |
| uncleaved VEGF trap | $4.93 \times 10^{-5} \pm 0.70\%$ | 3.9 |
| cleaved VEGF mini-trap | $5.46 \times 10^{-5} \pm 0.62\%$ | 3.53 |
| R1R2-myc myc his monomer | $6.74 \times 10^{-3} \pm 0.38\%$ | 0.028 |

Example 3

Construction of Plasmids Encoding VEGF Mini-Traps

VEGF mini-traps were constructed from a precursor of the parent VEGF trap, VEGFR1R2.FcΔC1(a) (SEQ ID NOs:7-8), in which the three amino acids glycine-alanine-proline served as a linker between the Flk1 D3 and FcΔC1(a). This plasmid, pTE115 was used in the construction of the VEGF mini-traps because the linker DNA sequence included a Srf I restriction endonuclease recognition sequence that facilitated engineering the VEGF trap. In all other respects, the VEGF trap encoded by pTE115 is identical to that of the VEGF trap, VEGFR1R2.FcΔC1(a) (SEQ ID NOs:7-8) described in detail in PCT publication WO/0075319.

Two VEGF mini-traps were constructed with multimerization domains consisting of either a single cysteine residue (R1R2$_C$) (SEQ ID NO:2) or the amino acids ACGC (SEQ ID NO:3) (R1R2$_{ACGC}$) (SEQ ID NO:4) added to the C-terminus of receptor components Flt1D2.Flk1D3. Both of these constructs are capable of forming homo-dimeric molecules stabilized by one (R1R2$_C$) or two (R1R2$_{ACGC}$) intermolecular disulfides.

The plasmid pTE517 was made by removing the 690 bp fragment generated by digestion of pTE115 DNA with Srf I and Not I and inserting the synthetic DNA fragment formed by annealing the oligos R1R2NC (SEQ ID NO:11) and R1R2CC (SEQ ID NO:12). The resulting plasmid encodes R1R2$_C$, which consists of the Flt1D2.Flk1D3 domains followed by a cysteine residue (SEQ ID NO:18). Similarly, the plasmid pTE518 was made by removing the 690 bp fragment generated by digestion of pTE115 DNA with Srf I and Not I, followed by ligation with the synthetic DNA fragment formed by annealing the oligos R1R2NACGC (SEQ ID NO:13) and R1R2CACGC (SEQ ID NO:14). The resulting plasmid encodes R1R2$_{ACGC}$, which consists of the Flt1D2.Flk1D3 domains followed by the amino acids ACGC (SEQ ID NO:20).

Plasmids were also constructed to direct the expression of these mini-traps in E. coli. The primers R1R2N-Nco1 (SEQ ID NO:15) and R1R2CNot1 (SEQ ID NO:16) were used to amplify a DNA fragment from pTE115 that encodes amino acids G30 to K231, relative to the parental VEGF trap (SEQ ID NO:8). Amplification of this sequence resulted in fusion of an initiating methionine codon at the 5' end and fusion of the codon for cysteine, followed by a stop codon, at the 3' end (SEQ ID NO:2). This DNA fragment was then cloned into the Nco I and Not I sites of the E. coli expression plasmid pRG663 to yield pRG1102 such that expression of R1R2$_C$ was dependent on transcription from the phage T7 Φ1.1 promoter. Induction of gene expression from pRG1102 results in accumulation of R1R2Cys in the cytoplasm of the E. coli host strain RFJ238. Similarly, the primers R1R2N-Nco1 (SEQ ID NO:15) and R1R2ACGC-N ot1 (SEQ ID NO:17) were used to amplify a DNA fragment from pTE115 that encodes amino acids G30 to K231 (SEQ ID NO:8) resulting in fusion of an initiating methionine codon at the 5' end and fusion of codons for ACGC (SEQ ID NO:3), followed by a stop codon, at the 3' end (SEQ ID NO:4). This fragment was then cloned into the Nco I and Not I sites of the E. coli expression plasmid pRG663 to yield pRG1103 such that expression of R1R2$_{ACGC}$ was dependent on transcription from the phage T7 Φ1.1 promoter. Induction of gene expression from both pRG1102 and pRG1103 resulted in accumulation of R1R2$_{C\,or\,R}$1R2$_{ACGC}$, respectively, in the cytoplasm of the E. coli host strain RFJ238.

Example 4

Purification and Characterization of VEGF Mini-Traps from E. coli

Both R1R2$_C$ and R1R2$_{ACGC}$ were expressed as cytoplasmic proteins in E. coli and were purified by the same method. Induction of the phage T7 Φ1.1 promoter on either pRG1102 or pRG1103 in the E. coli K12 strain RFJ238 resulted in accumulation of the protein in the cytoplasm. After induction, cells were collected by centrifugation, resuspended in 50 mM Tris-HCl, pH 7.5, 20 mM EDTA, and lysed by passage through a Niro-Soavi cell homogenizer. Inclusion bodies were collected from lysed cells by centrifugation, washed once in distilled H$_2$O, then solubilized in 8 M guanidinium-HCl, 50 mM Tris-HCl, pH 8.5, 100 mM sodium sulfite, 10 mM sodium tetrathionate and incubated at room temperature for 16 hours. Clarified supernatant was fractionated on an S300 column equilibrated with 6 M guanidinium-HCl, 50 mM Tris-HCl, pH 7.5. Fractions containing R1R2$_C$ were pooled and dialyzed against 6M Urea, 50 mM Tris-HCl, pH 7.5. Dialyzed protein was diluted to 2M Urea, 50 mM Tris-HCl, pH 8.5, 2 mM cysteine then stirred slowly for 7 days at 4° C. Refolded protein was dialyzed against 50 mM Tris-HCl, pH 7.5 then loaded onto an SP-sepharose column equilibrated with 50 mM Tris-HCl, pH 7.5 and eluted with a NaCl gradient from 0 to 1 M in 50 mM Tris-HCl, pH 7.5. Fractions containing R1R2$_C$ were pooled, concentrated, and loaded onto a Superdex 200 column equilibrated with 50 mM Tris-HCl, pH 7.5, 150 mM NaCl. Fractions containing mini-trap dimer were collected and pooled. The molecular weight of purified mini-trap was estimated to be about 46 kD by SDS-PAGE.

BIACORE™ assays were conducted (as described in WO/0075319) to determine trap affinity for VEGF, and the results showed that the R1R2$_C$ and R1R2$_{ACGC}$ mini-traps had VEGF affinity comparable to the full length VEGF trap (Table 2).

TABLE 2

| Trap | Kinetic Dissociation Rate (1/s) | $T_{1/2}$ (hr) |
| --- | --- | --- |
| VEGF trap | $4.23 \times 10^{-5}$ | 4.53 |
| R1R2$_C$ | $3.39 \times 10^{-5}$ | 5.68 |
| R1R2$_{ACGC}$ | $3.41 \times 10^{-5}$ | 5.65 |

Example 5

Expression of VEGF Mini-Traps in CHO K1 Cells

Expression of the VEGF mini-traps encoded by pTE517 and pTE518 is dependent on transcription from the human CMV-MIE promoter and results in secretion of the mini-traps into the culture medium when expressed in CHO cells. When expressed as secreted proteins in CHO K1, both mini-traps were found in the conditioned media and estimation of their molecular weight by SDS-PAGE suggested, as expected, that the proteins were glycosylated. Analysis by SDS-PAGE also indicated that the mini-traps were capable of forming homodimeric molecules stabilized by intermolecular disulfide(s) between the C-terminal cysteine(s). Specifically, the R1R2$_C$ mini-trap efficiently formed covalent dimers when expressed as a secreted protein in CHO cells.

Example 6

Construction and Expression of a Single Chain VEGF Mini-Trap

A VEGF mini-trap was also constructed that did not require a multimerization domain (SEQ ID NO:19). This mini-trap was constructed by direct fusion of one Flt1D2.Flk1D3 domain (R1R2) (amino acids 30-231 of SEQ ID NO:19) to a second Flt1D2.Flk1D3 domain (R1R2) (amino acids 234-435 of SEQ ID NO:19) with a Gly-Pro linker between the tandem receptor domains (amino acids 232-233 of SEQ ID NO:19).

To construct a gene encoding tandem Flt1D2.Flk1D3 domains, a DNA fragment was synthesized (Blue Heron Biotechnology) that encoded one Flt1D2.Flk1D3 domain that minimized DNA homology with the Flt1D2.Flk1D3 domain-encoding DNA found in pTE115. This synthetic DNA fragment was cloned as a Srf I-Not I fragment into the Srf I-Not I sites of pTE115 to yield pTE570, which expresses the R1R2-R1R2 VEGF mini-trap from the CMV-MIE promoter. When this plasmid is transfected into CHO K1 cells the R1R2-R1R2 VEGF mini-trap accumulates in the culture medium.

Example 7

Construction and Expression of a VEGF Mini-Trap

A VEGF mini-trap was constructed as described above, by direct fusion of one Flt1D2.Flk1D3 domain (R1R2) (amino acids 30-231 of SEQ ID NO:21) with a C-terminal nine amino acid sequence terminating in CPPC. When this plasmid is transfected into CHO K1 cells the VEGF mini-trap of SEQ ID NO:21 is secreted into the culture medium. Subsequent purification by non-reducing SDS-PAGE electrophoresis as well as native light-scattering analysis identified a trap molecule with molecular weight approximately 64 kDa. This molecular weight indicates that a covalent dimer was formed between two fusion polypeptides of SEQ ID NO:21. Similar experiments were conducted with plasmids encoding the fusion polypeptides of SEQ ID NOs:22 and 23, and similarly showed these molecules formed homodimeric traps. Affinity determinations for human VEGF-165 binding to EGF traps composed of dimers of SEQ ID NO:8 and SEQ ID NO:21 are shown in Table 3.

TABLE 3

| VEGF Trap | ka (1/Ms) | kd (1/s) | KD (M) |
| --- | --- | --- | --- |
| SEQ ID NO: 8 | $2.73 \times 10^{+7}$ | $1.79 \times 10^{-5}$ | $6.55 \times 10^{-13}$ |
| SEQ ID NO: 21 | $2.00 \times 10^{+7}$ | $6.56 \times 10^{-6}$ | $3.28 \times 10^{-13}$ |
| SEQ ID NO: 21 | $2.61 \times 10^{+7}$ | $5.77 \times 10^{-6}$ | $2.21 \times 10^{-13}$ |

Example 8

Glycosylation of VEGF-Binding Fusion Polypeptides

Sialic Acid Content. Sialic acid capping of carbohydrate chains has been identified as an important factor that lowers the clearance of glycoproteins from circulation. The total number of sialic acid residues in two batches, P3 and P3.5 (VGTC04003M500 and VGTC04008M500, respectively) of VEGF trap protein (amino acids 28-457 of SEQ ID NO:8) was determined using a quantitative HPLC assay. In this assay, sialic acid is released from the protein using mild acid hydrolysis, then derivatized with o-phenylenediamine, separated by HPLC, and measured by either UV or fluorescence detectors. Quantitation of sialic acid was assessed relative to a standard curve using sialyllactose. Fetuin is used as a positive control for the reaction. The total number of sialic acids released from the fusion polypeptide was 8-10 M and 9-10 M sialic acid/M of protein for P3 and P3.5, respectively.

Oligosaccharide Profiling by Normal-Phase Anion Exchange (NPAEC) HPLC. Oligosaccharide profiling was used to examine sugar chain quality of two batches of VEGF trap protein in both a qualitative and quantitative manner. PNGase F was used to remove N-linked sugar chains from the peptide backbone. These sugar chains were modified on the reducing end with anthranilic acid and separated by charge through ion exchange chromatography. Chains containing no sialic acid moieties were eluted separately from chains with a single sialic acid, chains with 2 sialic acids, and chains with 3 sialic acids, etc. Peak areas were determined for each sugar chain species and quantified relative to the total peak area of all chain species. The Z number was calculated from the sum of the areas of the single sialic acid containing chains plus 2 times the area of the two sialic acid containing species plus 3 times the area of the three sialic acid containing species (etc) divided by the sum of the total peak area. The higher the Z number, the greater the extent of average sialic acid on the oligosaccharide chains. The calculated Z numbers were 1.1 (P3) and 1.0 (P3.5).

Capillary Electrophoresis Fingerprinting. A quantitative oligosaccharide fingerprint assay was developed using capillary electrophoresis (CE) to examine differences in sugar chain structure between protein lots. Unlike the ion exchange (IE) method used to evaluate the sialic acid oligosaccharide profile, the CE method can more readily separate oligosaccharide chains with equivalent charge. The fusion polypeptide were denatured, and then deglycosylated by addition of PNGase to release N-linked sugar chains. The samples were incubated overnight at 37° C., then spiked with maltose (Fluka) as an internal standard. Released sugar chains were chemically modified in a solution containing the fluorophore labeling reagent, 8-aminopyrene 1,2,6-trisulfonate (APTS).

Following modification, the released and labeled oligosaccharides were separated by capillary electrophoresis. Structural assignments for the biantennary structures were based on comigration with synthetic oligosaccharide standards. Other carbohydrate species corresponding to triantennary forms have not yet been assigned, but they constitute a very small fraction of the total carbohydrate. Analysis of electropherograms did not reveal any unique sugar chain peaks.

Oliciosaccharide Analysis by MALDI-TOF MS. A global measurement of all the N-linked sugar chains by mass spectrometry was performed on two batches of the VEGF trap. Oligosaccharides were released by PNGase F, derivatized with anthranilic acid, precleaned by SPE HLB cartridge. The oligosaccharides were further cleaned with DOWEX® AG-50w×12 resin prior to MALDI analysis. Spectra were collected in negative linear mode. The mass spectrum of each oligosaccharide pool was determined and the structural assignments made (FIGS. 1A-C). The expected masses are the average mass calculated based on the proposed N-linked sugar chains with addition of anthranilic acid derivatization. The monosaccharide compositions are listed based on the proposed N-linked sugar chain structures as well.

Oligosaccharide Chain Structures on Individual Glycosylation Sites by Electrospray Ionization-Mass Spectrometry (ESI-MS). The carbohydrate structures on each individual glycosylation site of two batches of VEGF trap (P3 and P3.5) were determined by a peptide mapping approach. The protein samples were reduced and blocked with iodoacetamide. The samples were then digested with trypsin and the peptides mixture were analyzed by LC/MS. Glycopeptides typically elutes as a group of poorly resolved peaks on HPLC chromatogram and recognized by its characteristic mass patterns. Sugar chain masses were calculated from observed glycopeptide masses. The following sugar chain structures were observed based on mass match: Asn62 and Asn94 were mainly fucosylated bi-antennary, with 0-2 sialic acid and smaller amount of non-fucosylated; Asn94 was partially glycosylated to a similar extent; Asn149 and Asn222 were mainly non-fucosylated bi-antennary, with 0-2 sialic acid, and smaller amount of fucosylated bi-antennary, Man-5, and hybrid type sugar chains; Asn308 was mainly fucosylated bi-antennary, with no sialic acid and smaller amount of non-fucosylated form.

Other features of the invention will become apparent in the course of the following descriptions of exemplary embodiments which are given for illustration of the invention and are not intended to be limiting thereof.

We claim:

1. A recombinant nucleic acid molecule encoding a fusion polypeptide R1-R2-F, wherein R1 is vascular endothelial cell growth factor (VEGF) receptor component Ig domain 2 of Flt-1 (amino acids 27-129 of SEQ ID NO:8), R2 is Ig domain 3 of Flk-1 (amino acids 130-231 of SEQ ID NO:8), and F is a truncated multimerizing component selected from the group consisting of amino acids 232-458, 232-457, 352-458 and 352-457 of SEQ ID NQ:8.

2. A vector comprising the nucleic acid molecule of claim 1.

3. A method of producing a VEGF fusion polypeptide, comprising the steps of introducing into a suitable host cell the vector of claim 2, and effecting expression of the VEGF fusion polypeptide.

4. The method of claim 3, wherein the host cell is a mammalian cell.

5. The method of claim 4, wherein the mammalian cell is a CHO cell.

6. A fusion polypeptide produced by the method of claim 5 comprising amino acids 28-457 of SEQ ID NO:8 which is glycosylated at Asn residues at positions 62, 94, 149, 222 and 308.

7. A multimer comprising two or more of the fusion polypeptides of claim 6.

8. The multimer of claim 7 which is a dimer capable of binding VEGF with an affinity (Kd) of at least $1 \times 10^{-10}$ M.

9. The dimer of claim 8 wherein the Kd is at least $1 \times 10^{-11}$ M.

10. The dimer of claim 9, wherein the Kd is at least $1 \times 10^{-12}$ M.

11. A pharmaceutical composition comprising the VEGF trap of claim 10, and a pharmaceutically acceptable carrier.

* * * * *